(12) United States Patent
Donovan et al.

(10) Patent No.: US 9,868,943 B2
(45) Date of Patent: Jan. 16, 2018

(54) **ENHANCED STAPHYLOLYTIC ACTIVITY OF THE *STAPHYLOCOCCUS AUREUS* BACTERIOPHAGE VB_SAUS-PHILPLA88 VIRION-ASSOCIATED PEPTIDOGLYCAN HYDROLASE HYDH5: FUSIONS, DELETIONS AND SYNERGY WITH LYSH5**

(71) Applicant: The United States of America, as Represented by the Secretary of Agriculture, Washington, DC (US)

(72) Inventors: David M. Donovan, Baltimore, MD (US); Lorena Rodriguez Rubio, Austrias (ES); Beatriz Martinez Fernandez, Austrias (ES); Ana Rodriguez, Austrias (ES); Pilar Garcia Suarez, Austrias (ES)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 14/621,120

(22) Filed: Feb. 12, 2015

(65) Prior Publication Data
US 2015/0247138 A1  Sep. 3, 2015

Related U.S. Application Data

(62) Division of application No. 13/298,966, filed on Nov. 17, 2011, now Pat. No. 8,986,695.

(51) Int. Cl.
| | |
|---|---|
| *A61K 39/40* | (2006.01) |
| *C12N 9/48* | (2006.01) |
| *A61K 38/54* | (2006.01) |
| *C12N 9/14* | (2006.01) |
| *C12N 9/52* | (2006.01) |
| *A61K 38/47* | (2006.01) |
| *A61K 38/48* | (2006.01) |

(52) U.S. Cl.
CPC .............. *C12N 9/485* (2013.01); *A61K 38/47* (2013.01); *A61K 38/4813* (2013.01); *A61K 38/4886* (2013.01); *A61K 38/54* (2013.01); *C12N 9/14* (2013.01); *C12N 9/52* (2013.01); *C07K 2319/00* (2013.01); *C12Y 302/01017* (2013.01); *C12Y 304/19011* (2013.01); *C12Y 304/24075* (2013.01)

(58) Field of Classification Search
None
See application file for complete search history.

(56) References Cited

U.S. PATENT DOCUMENTS

2010/0158886 A1* 6/2010 Donovan ................. C12N 9/52
424/94.3

OTHER PUBLICATIONS

Donovan et al. II (Applied and Environmental Microbiology, vol. 72, No. 4, pp. 2988-2996, 2006).*
Rodriguez et al. . BMC Microbiology vol. 11 No. 138, Jun. 17, 2011.*

* cited by examiner

*Primary Examiner* — Ja'Na Hines
*Assistant Examiner* — Khatol Shahnan Shah
(74) *Attorney, Agent, or Firm* — John D. Fado; Mark D. McNemar

(57) ABSTRACT

Virion-associated peptidoglycan hydrolases have a potential as antimicrobial agents due to their ability to lyse Gram positive bacteria on contact. Fusion proteins HydH5SH3b and HydH5Lyso comprising full-length peptidoglycan hydrolase HydH5 from the *Staphylococcus aureus* bacteriophage vB_SauS-phi-IPLA88 in combination with the SH3 cell wall-binding domain from lysostaphin or full length lysostaphin, respectively, exhibited high lytic activity against live *S. aureus* cells. CHAPSH3b, a HydH5 CHAP (cysteine, histidine-dependent amidohydrolase/peptidase) domain from truncated HydH5 in combination with the SH3b domain of lysostaphin, exhibited the highest lytic activity against live *S. aureus* cells. HydH5 and its derivative fusions lysed bovine and human *S. aureus*, methicillin-resistant *S. aureus* (MRSA) N315 strain, and human *S. epidermidis* strains in zymogram, plate lysis and turbidity reduction assays. HydH5 and its derivative fusions displayed antimicrobial synergy with the endolysin LysH5 (also encoded by vB_SauS-phi-IPLA88) in vitro suggesting the two enzymes have distinct cut sites and thus may be more efficient in combination for elimination of staphylococcal infections.

5 Claims, 5 Drawing Sheets

ENHANCED STAPHYLOLYTIC ACTIVITY OF THE *STAPHYLOCOCCUS AUREUS* BACTERIOPHAGE VB_SAUS-PHILPLA88 VIRION-ASSOCIATED PEPTIDOGLYCAN HYDROLASE HYDH5: FUSIONS, DELETIONS AND SYNERGY WITH LYSH5

This application is a divisional application of application Ser. No. 13/298,966 filed Nov. 17, 2011, now pending, which is herein incorporated by reference in its entirety.

BACKGROUND OF THE INVENTION

Field of the Invention

This invention relates to the field of polypeptides having antimicrobial activity and the polynucleotides encoding them. The invention also relates to nucleic acid constructs, vectors, and host cells comprising the nucleic acid constructs. The invention more specifically relates to an antimicrobial phage-associated HydH5 peptidoglycan hydrolase polypeptide, truncations of the HydH5 peptidoglycan hydrolase polypeptide, and fusion polypeptides comprising the HydH5 peptidoglycan hydrolase and truncated HydH5 polypeptides. This invention also relates to synergistic pathogen-specific compositions comprising the endolysin LysH5 together either with HydH5 or with fusion polypeptides comprising HydH5. The invention further relates to compositions and methods of making the polypeptides and methods of treating staphylococcal-associated diseases, including methicillin-resistant *Staphylococcus aureus* (MRSA).

Description of the Relevant Art

*Staphylococcus aureus* is a notorious pathogen that causes numerous pathologies including food poisoning, toxic shock syndrome, endocarditis, and skin and wound infections, (Lowy, F. D. 1998. *N. Engl. J. Med.* 339:520-532). The emergence of multidrug-resistant strains, especially methicillin-resistant *S. aureus* (MRSA) and vancomycin-resistant *S. aureus* (VRSA) is raising serious concerns due to their high frequency in both nosocomial and community-acquired settings (Köck et al. 2010. *Euro Surveill.* 15(41):19688).

Recent results with phage therapy in animal models have driven much interest in phages and phage-encoded proteins to treat infections (O'Flaherty et al. 2009. FEMS Microbiol. Rev. 33(4):801-819; Fenton et al. 2010. *Bioeng. Bugs.* 1(1):9-16). These studies clearly show the efficacy of phages and lysins in killing human pathogenic bacteria in animal models (Matsuzaki et al. 2005. *J. Infect. Chemotherapy* 11:211-219; Fischetti, V. A. 2010. *Int. J. Med. Microbiol.* 300(6):357-362). Specifically, several assays have been performed against *S. aureus* bacteremia. The intraperitoneal administration of phages phiMR11 and phiMR25 rescued mice inoculated with a lethal dose of *S. aureus* (Matsuzaki et al. 2003. *J. Infect. Dis.* 187(4):613-624; Hoshiba et al. 2010. *Arch. Virol.* 155(4):545-552). Moreover, in a rabbit model of wound infection caused by *S. aureus*, phages prevented abscess formation (Wills et al. 2005. *Antimicrob. Agents Chemother.* 49(3):1220-1221). Phage lytic proteins also showed successful results. The intraperitoneal administration of the endolysin MV-L from phage phiMR11 protected mice against *S. aureus* MRSA septic death (Rashel et al. 2007. *J. Infect. Dis.* 196(8):1237-1247). In another animal model, bacteremia in unprotected mice reached colony counts of $\sim 10^7$ cfu/ml within 3.5 h after challenge, whereas the administration of the lytic enzyme LysGH15 1 h after MRSA injection was sufficient to protect mice with the mean colony count being less than $10^4$ cfu/ml (Gu et al. 2011. *J. Clin. Microbiol.* 49(1):111-117). Furthermore, the activity of phage lytic proteins may be increased by using them in combination with other antimicrobials. Both in vitro (Becker et al. 2008. *FEMS Microbiol. Lett.* 287(2):185-191; Daniel et al. 2010. *Antimicrob. Agents Chemother.* 54(4):1603-1612; García et al. 2010. *Int. J. Food Microbiol.* 141 (3):151-155) and in vivo synergy (Daniel et al., supra) between phage endolysin constructs and antibiotics or bacteriocins against *S. aureus* have been reported.

Bacterial cell walls of both Gram-positive and Gram-negative bacteria are composed of peptidoglycan, a complex molecule with a sugar backbone of alternating N-acetylglucosamine and N-acetyl muramic acid residues cross-linked with peptide bridges. Peptidoglycan prevents osmotic lysis of cell protoplast and confers rigidity and shape on cells. Peptidoglycan hydrolases are essential for modifying the peptidoglycan to allow the cell to grow and divide (Vollmer et al. 2008. *FEMS Microbiol. Rev.* 32(2):287-306). There are three major peptidoglycan hydrolase activities, namely, (i) glycosidase, (ii) amidase, and (iii) endopeptidase activities. Most peptidoglycan hydrolases are composed of a C-terminal cell wall-binding (CWB) domain and a N-terminal catalytic domain(s) (Fischetti, V. A. 2005. *Trends in Microbiol.* 13:491-496). Bacteriophages also encode peptidoglycan hydrolases (Hermoso et al. 2007. *Curr. Opin. Microbiol.* 10(5):461-472) that play essential roles in the phage life cycle to allow both entry (virion-associated peptidoglycan hydrolases) and release (endolysins) of the mature phage particles.

In addition to endolysins, other phage encoded proteins (virion-associated peptidoglycan hydrolases) have a potential as antimicrobials. Some bacteriophage virions harbor virion-associated peptidoglycan hydrolases that facilitate the entry of phage DNA across the bacterial cell envelope during infection (Moak and Molineux. 2004. *Mol. Microbiol.* 51:1169-1183). They are also responsible for the "lysis from without", a phenomenon caused by some phages when adsorbed onto the host cell at very high numbers (Delbrück, M. 1940. *J. Gen. Physiol.* 23(5):643-660). This type of peptidoglycan hydrolase activity has been described from a variety of different phage particles infecting *S. aureus* (Moak and Molineux, supra; Rashel et al. 2008. *FEMS Microbiol. Lett.* 284:9-16; Takac and Blasi. 2005. *Antimicrob. Agents Chemother.* 49(7):2934-2940), *Lactococcus lactis* (Kenny et al. 2004. *J. Bacteriol.* 186:3480-3491), *E. coli* (Molineux, I. J. 2001. *Mol. Microbiol.* 40:1-8; Kanamaru et al. 2002. *Nature* 415:553-557), and *Salmonella* (Steinbacher et al. 1997. *J. Mol. Biol.* 267:865-880).

Recently, a peptidoglycan hydrolase (HydH5) encoded by phage vB_SauS-phiIPLA88 (phiIPLA88) has been identified and characterized (Rodríguez et al. 2011, *BMC Microbiol.* 11: 138). HydH5 has a N-terminal CHAP (cysteine, histidine-dependent amidohydrolase/peptidase) lytic domain and a C-terminal LYZ2 (lysozyme subfamily 2) lytic domain. HydH5 does not have a recognized cell wall binding domain. The full-length 634 amino acid HydH5 and truncated version harboring just one lytic domain (and 6xHis-tag) have been overproduced in *E. coli*. The nickel chromatography purified proteins are able to kill viable *S. aureus* cells. HydH5 is highly thermostable since it showed antimicrobial activity after heat treatment (100° C., 5 min) (Rodríguez et al., supra).

Lysostaphin is a bacteriocin secreted by *S. simulans* that lyses *S. aureus* (Browder et al. 1965. *Biochem. Biophys. Res. Commun.* 19: 389). The endopeptidase activity is specific to the glycyl-glycyl bonds of the staphylococcal peptidoglycan inter-peptide bridge. It is known that lysostaphin can kill planktonic *S. aureus* (Walencka et al. 2005. *Pol. J. Microbiol.* 54: 191-200; Wu et al. 2003. *Antimicrob. Agents Chemother.* 47: 3407-3414), as well as MRSA (Dajcs et al. 2000. *Am. J. Ophthalmol.* 130: 544), vancomycin-intermediate *S. aureus* (Patron et al. 1999. *Antimicrob. Agents Chemother.* 43:1754-1755), and other antibiotic-resistant strains of *S. aureus* (Peterson et al. 1978. *J. Clin. Invest.* 61: 597-609). Lysostaphin can also kill *S. aureus* growing in a biofilm (Walencka, supra; Wu, supra), and it exhibits limited activity against coagulase-negative staphylococci (Cisani et al. 1982. *Antimicrob. Agents Chemother.* 21: 531-535); McCormick et al. 2006. *Curr. Eye Res.* 31: 225-230).

The endolysin LysH5 is encoded by phiIPLA88 phage and has three putative domains: a cysteine, histidine-dependent amidohydrolases/peptidase (CHAP) domain, an amidase-2 domain, and a C-terminal SH3b cell wall-binding (CWB) domain. LysH5 is able to inhibit the *S. aureus* growth in milk (Obeso et al. 2008. *Int. J. Food Microbiol.* 128(2):212-218) and showed a synergistic antimicrobial effect with the bacteriocin nisin (García et al. 2010, supra).

Antibiotic resistance in combination with other important virulence determinants, such as surface-located binding proteins to facilitate adhesion to host tissue, as well as many mechanisms to evade attack by human host defenses makes *S. aureus* a threatening pathogen (Otto, M. 2010. *Ann. Rev. Microbiol.* 64:143-162). Novel therapeutic agents specific for staphylococcal species, including methicillin-resistant *Staphylococcus aureus* (MRSA), are sorely needed to counter the rise of drug resistant pathogenic bacteria.

SUMMARY OF THE INVENTION

We have discovered that the nucleic acid encoding the vB_SauS-phiIPLA88 virion-associated peptidoglycan hydrolase HydH5, a protein which specifically attacks the peptidoglycan cell wall of untreated live staphylococci can be truncated, that truncations encoding the CHAP (cysteine, histidine-dependent amidohydrolase/peptidase) lytic domain of the HydH5 peptidoglycan hydrolase result in polypeptides capable of exolysis, i.e., "lysis from without" lytic activity, and that truncations of HydH5 and fusion polypeptides comprising HydH5 or truncations of HydH5 can be used as an antimicrobial treatment for Staphylococcal-induced infection and diseases, including infection and disease caused by multidrug-resistant strains.

In accordance with this discovery, it is an object of the invention to provide nucleic acid molecules encoding the truncated HydH5 polypeptides and fusion proteins comprising the HydH5 peptidoglycan hydrolase polypeptide and truncations of HydH5.

It is also an object of the invention to provide an antimicrobial truncated HydH5 peptidoglycan hydrolase polypeptide which is functional in that it comprises the CHAP domain and retains its properties for exolysis of the peptidoglycan cell wall of staphylococcal bacteria.

It is a further object of the invention to provide polynucleotides encoding antimicrobial fusion proteins formed from a nucleic acid encoding a non-truncated HydH5 peptidoglycan hydrolase or encoding a truncated HydH5, i.e., a functioning CHAP domain, in combination with a nucleic acid encoding lysostaphin or one or more of the SH3 cell wall-binding domain(s) of native lysostaphin.

It is a further object of the invention to provide antimicrobial fusion proteins comprising either a non-truncated HydH5 peptidoglycan hydrolase or a functioning HydH5 CHAP domain from truncated HydH5 in combination with either lysostaphin or one or more of the SH3b cell wall-binding (CWB) domain(s) of native lysostaphin, i.e., HydH5 peptidoglycan hydrolase-lysostaphin, HydH5 peptidoglycan hydrolase-SH3b, and HydH5CHAP-SH3b.

It is another object of the invention to provide a method of using antimicrobial fusion proteins comprising the CHAP domain from truncated HydH5 peptidoglycan hydrolase in combination with lysostaphin or a SH3b cell wall-binding domain from lysostaphin to enhance the exolysis of *Staphylococcus* strains and also extend the targets that can be "lysed from without" to additional bovine and human strains of *Staphylococcus* over and above the lysis observed with functional native HydH5 peptidoglycan hydrolase comprising the native N-terminal CHAP domain in combination with the native C-terminal LYZ2 (lysozyme subfamily 2) lytic domain.

An added object of the invention is to provide a nucleic acid sequence encoding an antimicrobial HydH5 fusion polypeptide comprising the nucleic acid encoding the HydH5 peptidoglycan hydrolase or the truncated HydH5 peptidoglycan hydrolase, i.e., the CHAP domain, in combination with nucleic acid encoding lysostaphin or a SH3b cell wall-binding domain from lysostaphin according to the invention as an encoding sequence which allows disease resistance to be imparted to the organism. It is well understood that this sequence can also be used in combination with another sequence, or sequences, encoding one or more disease resistant properties.

An additional object of the invention is to provide nucleic acid constructs, vectors, and host cells comprising the nucleic acid constructs encoding the fusion polypeptides of the invention.

An added object of the invention is to provide compositions useful for the treatment of disease caused by the *Staphylococcus* strains for which the fusion proteins of the invention are specific and effective.

Another object of the invention is to provide compositions comprising the LysH5 endolysin together with HydH5 peptidoglycan hydrolase or with an HydH5-derived fusion protein selected from HydH5 peptidoglycan hydrolase-lysostaphin, HydH5 peptidoglycan hydrolase-SH3b, or HydH5CHAP-SH3b for treatment of diseases and infections caused by *Staphylococcus* strains where the composition comprises LysH5 and a particular HydH5 fusion protein each in amounts that are ineffective alone but act synergistically together to effectively treat said diseases and infections.

Also part of this invention is a kit, comprising a composition for treatment of disease caused by the *Staphylococcus* strains for which the CHAP domain of the truncated HydH5 peptidoglycan hydrolase and fusions comprising the truncated HydH5 peptidoglycan hydrolase CHAP domain are specific and effective.

Other objects and advantages of this invention will become readily apparent from the ensuing description.

BRIEF DESCRIPTION OF THE DRAWINGS

FIG. 2A shows the SDS-PAGE and zymogram analyses of 5 μg nickel affinity-purified proteins. Lane M: Standard molecular mass marker in kDa (Prestained SDS-PAGE Standards, broad range; BioRad Laboratories); lane 1, CHAP (19.6 kDa); 2, HydH5 (73.6 kDa); 3, HydH5SH3b (85.1 kDa); 4, HydH5Lyso (100.8 kDa); 5, CHAPSH3b (30.4 kDa); 6, Lysostaphin (28.1 kDa). FIG. 2B shows a plate lysis assay of HydH5 and derived proteins using mid-log phase growing cells of S. aureus Sa9 and MRSA strain N315. FIG. 2C shows turbidity reduction assay results using 1 µM of each protein. Specific activity is expressed as $\Delta OD_{600\,nm}$ $min^{-1}$ $\mu M^{-1}$. Error bars are the means±standard deviations of three independent assays.

DETAILED DESCRIPTION OF THE INVENTION

Figure 1:
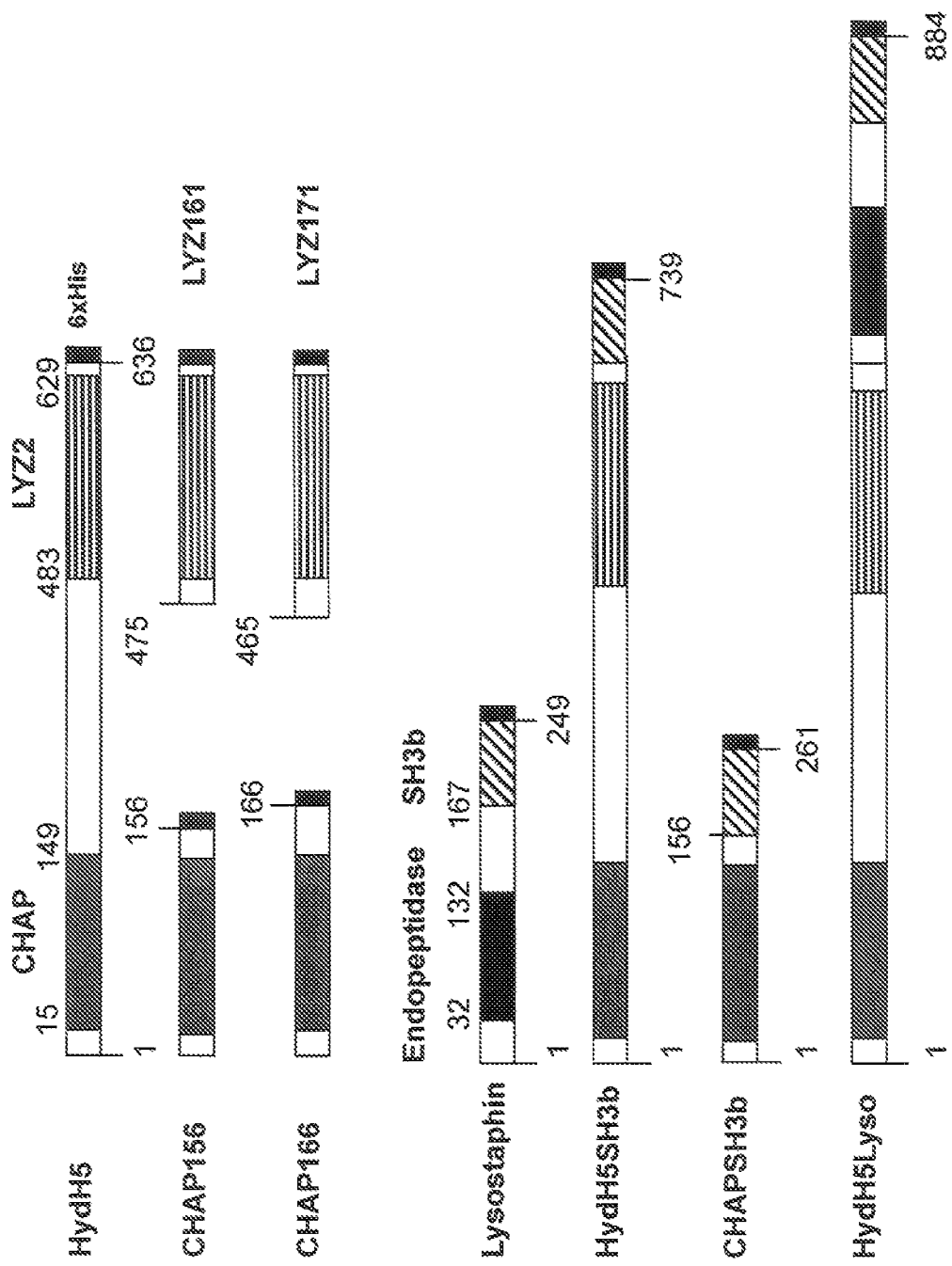
FIG. 1 is a schematic representation of HydH5 deletion and fusion constructs. The numbers indicate the initial and final amino acids in the domains as determined by Pfam domain database. Grey box: CHAP domain; horizontal stripes: LYZ2 domain; diagonal stripes=SH3b domain; large black box: endopeptidase domain; small black box: 6×His-tag.

In order to enhance the native antimicrobial activity of HydH5 peptidoglycan hydrolase against target staphylococcal species and strains, in this work we have fused HydH5 to both full length and truncated fragments of lysostaphin, a staphylolytic bacteriocin produced by *Staphylococcus simulans*. A chimeric protein made up of complete HydH5 and lysostaphin fused in a head to tail configuration was created. Similarly, both the complete HydH5 protein and just the HydH5 CHAP domain were fused to the SH3b CWB domain of lysostaphin in two separate constructs. The enzybiotic activity of all these fusion proteins towards live *S. aureus* and numerous non-staphylococcal bacteria was assessed. The list of pathogen species effectively lysed by proteins encoded by the constructs of invention has been extended to include both bovine and human staphylococcal strains. Finally, we have also evaluated possible synergistic effects between HydH5 and the endolysin LysH5 with the purpose to explore new enzybiotic-based strategies to fight *S. aureus* infections.

In our previous work (Rodríguez et al. 2011, supra), we demonstrated the antimicrobial activity of HydH5 peptidoglycan hydrolase against *S. aureus* Sa9 strain. With the goal to increase the HydH5 lytic activity we performed deletion analysis and created fusion proteins with the most active deletion constructs. Through deletion analysis we had identified in HydH5 the protein domains that are essential for its activity and showed that both CHAP and LYZ2 domains possess lytic activity against *S. aureus* cells (Rodríguez et al. 2011, supra). Previous to this work several reports have shown that endolysins can be truncated and some individual catalytic domains retain lytic activity with some of them showing higher specific activity than the full length protein (Cheng et al. 2007. *Appl. Microbiol. Biotechnol.* 74(6):1284-1291; Horgan et al. 2009. *Appl. Environ. Microbiol.* 75(3): 872-874; Donovan et al. 2006. *Appl. Environ. Microbiol.* 72:5108-5112; Becker et al. 2008, supra). However, as was previously shown, some endolysin catalytic domains are almost inactive, such as the glycosidase domains from lambdaSa2 prophage endolysin (Donovan and Foster-Frey. 2008. *FEMS Microbiol. Lett.* 287(1):22-33), or the B30 endolysin (Donovan et al. 2006, supra) and the amidase domain from LysK (Becker et al. 2008, supra). Although there might be protein stability or aberrant protein folding influencing our results, the HydH5 CHAP domain construct has approximately 1.4-fold lower specific activity compared to the activity of the full length HydH5, suggesting that LYZ2 domain also contributes to the complete protein activity.

We and others have shown previously that virion-associated peptidoglycan hydrolases lacking a defined CWB domain can also bind to the cell surface (Rashel et al. 2008, supra; Rodríguez et al. 2011, supra). Known CWB domains have been shown for some peptidoglycan hydrolases to be necessary for accurate cell wall recognition and subsequent lytic activity such as lysostaphin (Baba and Schneewind. 1996. *EMBO J.* 15(18):4789-4797), ALE-1 (Lu et al. 2006. *J. Biol. Chem.* 281(1):549-558), *L. monocytogenes* endolysins Ply118 and Ply500 (Loessner et al. 2002. *Mol. Microbiol.* 44(2):335-349) and *S. pneumoniae* CPL-1 (Pérez-Dorado et al. 2007. *J. Biol. Chem.* 282(34):24990-24999). However, there are numerous reports of C-terminally deleted lysin constructs with deleted CWB domains where the N-terminal lytic domain maintains its activity in the absence of its CWB domain (Cheng et al., supra; Sass and Bierbaum. 2007. *Appl. Environ. Microbiol.* 73(1):347-352; Horgan et al., supra; Donovan et al. 2006, supra; Becker et al. 2008, supra). Thus a defined CWB domain is not a necessity for full lytic activity, and this binding does not rule out the possibility that the inter-lytic domain region might harbour a heretofore unidentified CWB domain as suggested previously for the B30 endolysin (Donovan et al. 2006, supra; lysostaphin/B30 fusion).

Our hypothesis to justify the addition of a CWB domain considers the fact that a phage structural protein, HydH5, is likely brought into close proximity of the cell wall and the peptidoglycan substrate by the intact virion, meaning that a CWB domain is likely not a strict requirement. However, as a soluble single protein antimicrobial, the scenario is quite different and the addition of a CWB domain might improve its lytic activity. Our SDS PAGE and zymogram results show that for all constructs, we are working with >95% pure proteins. In the HydH5-SH3b construct, the lysostaphin SH3b domain was fused to full-length HydH5 increasing the lytic activity 1.7-fold, suggesting that this CWB domain helps the lytic domain to degrade the peptidoglycan substrate. A similar result was obtained when the native Cpl-7 cell wall binding domains of the streptococcal LambdaSa2 endolysin was replaced by staphylococcal SH3b domain from lysostaphin or LysK resulting in a 5× increase in staphylolytic activity (Becker et al. 2009. *FEMS Microbiol. Lett.* 294(1):52-60). In the HydH5CHAP-SH3b construct, the lysostaphin SH3b domain was fused to the CHAP domain of HydH5 resulting in a 4.8-fold increase in the lytic activity of the CHAP domain alone construct (CHAP) and a 3.3-fold increase compared to full length HydH5. This result indicates the importance of the SH3b CWB domain in recognizing the bacteria cell wall, taking into account that only one catalytic domain (CHAP) fused to the SH3b domain was sufficient to obtain the highest specific activity of the various constructs.

Moreover, addition of the full length lysostaphin to HydH5 (HydH5-lysostaphin) also achieved greater activity levels than the parental protein (HydH5). This result further indicates the modular nature of these protein domains and that the addition of new catalytic domains to HydH5 (i.e., the glycyl-glycine endopeptidase of lysostaphin) can also improve its lytic activity. The three different catalytic domains are believed to each attack a different peptidoglycan bond. The presence of multiple unique domains theoretically decreases the likelihood of bacterial resistance development (Fischetti, V. A. 2005, supra). The increased activity also suggests that each domain is modular, as expected (Garcia et al. 1990. Gene 86(1):81-88), and although the activity of the final construct is not the sum of parental lytic activities, each domain likely achieves a near-native conformation.

HydH5 and its derivatives fusions were assessed for their ability to lyse a number of staphylococcal and non-staphylococcal strains. No previous data have been reported regarding the lytic spectrum of *S. aureus* virion-associated peptidoglycan hydrolases. All proteins were active against staphylococcal strains but no other genus was lysed at detectable levels. Our results indicate a similar lytic spectrum for both HydH5 and its derivative fusions. These results are in agreement with *S. aureus* endolysins described to date that demonstrate a lytic spectrum limited to staphylococci. However, a different level of the lytic activity was observed for each species/strain. In general, *S. aureus* strains were more sensitive than *S. epidermidis* strains. Within the *S. aureus* strains, we observed that bovine strains were more sensitive than clinical strains. This could be due to the shared origin of these strains and the phage from which HydH5 originated; both share a source from a dairy environment. A similar result was previously observed for endolysin LysH5 (Obeso et al., supra). Although we do not yet have direct biochemical proof that all three lytic domains are functional in the HydH5-lysostaphin construct, the reduced activity against *S. epidermidis* compared to *S. aureus* is consistent with the lytic range of lysostaphin and suggests that the lysostaphin domain is functional in this construct, given that lysostaphin is known to have a reduced activity against *S. epidermidis* compared to *S. aureus* (Zygmunt et al. 1968. *Appl. Microbiol.* 16(8):1168-1173).

Synergistic interactions between antimicrobial compounds have the potential to be exploited in order to increase effectiveness against the target bacteria, thereby reducing the dose required of each while decreasing the likelihood of antimicrobial-resistance. The combination of the two lytic bacteriophage enzymes HydH5 and LysH5 appears to have synergistic activity on *S. aureus* Sa9 strain. The HydH5-derived fusions also showed this positive interaction. The basis of synergy between peptidoglycan hydrolases might be explained by the hydrolytic activity of one enzyme loosening the peptidoglycan structure, thus facilitating better access of the second enzyme to its target. It is encouraging that the strongest in vitro synergy was observed between LysH5 and HydH5-lysostaphin, suggesting that this combination might be protective in vivo. However, in the absence of biochemical data to indicate which domains are active in the fusion and the parental LysH5, we cannot identify the particular domains that are responsible for the observed antimicrobial synergy. However, these results are in agreement with previous studies indicating synergy between Pal and Cpl-1 lysins against *S. pneumoniae* (Loeffler and Fischetti. 2003. *Antimicrob. Agents Chemother.* 47(1):375-377), and the synergy between endolysin LysK and the bacteriocin lysostaphin against *S. aureus*. A 33% reduction in LysK concentration was obtained in the presence of lysostaphin (Becker et al. 2008, supra). Another bacteriocin, nisin, enhanced 8-fold the lytic activity of LysH5 on *S. aureus* cell suspensions (García et al. 2010, supra). Comparable results were obtained by combination with antibiotics (Manoharadas et al. 2009. *J. Biotechnol.* 139:118-123; Daniel et al., supra). However, the effect of a second antimicrobial compound on reducing the development of resistant staphylococcal strains is also a consideration.

In summary, we report the development of novel chimeric peptidoglycan hydrolases with improved lytic activity against *S. aureus* and *S. epidermidis*, including MRSA N315 strain. The effectiveness of HydH5 and its derivative fusions when used in combination with LysH5, another dairy-derived protein were remarkable. We expect that these constructs will provide new weapons to combat multidrug-resistant *S. aureus* infections in both dairy and clinical environments.

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding an isolated truncated HydH5 peptidoglycan hydrolase related protein (truncation or fusion) as defined above. By host organism there is to be understood any single-celled or lower or higher non-human multi-celled organism into which HydH5 peptidoglycan hydrolase gene according to the invention can be introduced. The regulatory elements required for expressing the nucleic acid sequence encoding a truncated HydH5 peptidoglycan hydrolase are well known to those skilled in the art and depend on the host organism. The means and methods for identifying and choosing the regulatory elements are well known to those skilled in the art and widely described in the literature.

The present invention also relates to a cloning and/or expression vector for transforming a host organism containing at least the truncated HydH5 peptidoglycan hydrolase gene as defined hereinabove. This vector comprises, in addition, to the above truncated HydH5 peptidoglycan hydrolase gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the HydH5 peptidoglycan hydrolase according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment.

However, isolated polynucleotides may contain polynucleotide sequences which may have originally existed as extrachromosomal DNA but exist as a nucleotide insertion within the isolated polynucleotide. Isolated polynucleotides may be purified from a host cell in which they occur. Conventional nucleic acid methods known to skilled artisans may be used to obtain isolated polynucleotides. The term embraces cDNA, recombinant polynucleotides and chemically synthesized polynucleotides.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence (s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional fragments of the HydH5 peptidoglycan hydrolase polypeptide and functional fusion polypeptides encompassing a functional HydH5 peptidoglycan hydrolase and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of HydH5 peptidoglycan hydrolase" refers to all fragments of HydH5 peptidoglycan hydrolase that retain HydH5 peptidoglycan hydrolase activity and function to lyse staphylococcal bacteria.

Modifications of the HydH5 peptidoglycan hydrolase primary amino acid sequence may result in further mutant or variant proteins having substantially equivalent activity to the HydH5 peptidoglycan hydrolase polypeptides described herein. Such modifications may be deliberate, as by site-directed mutagenesis, or may occur by spontaneous changes in amino acid sequences where these changes produce modified polypeptides having substantially equivalent activity to the HydH5 peptidoglycan hydrolase polypeptide. Any polypeptides produced by minor modifications of the HydH5 peptidoglycan hydrolase primary amino acid sequence are included herein as long as the biological activity of HydH5 peptidoglycan hydrolase is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a HydH5 peptidoglycan hydrolase polypeptide and which hybridize under stringent conditions to the HydH5 peptidoglycan hydrolase sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have HydH5 peptidoglycan hydrolase-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the HydH5 peptidoglycan hydrolase polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, HydH5 peptidoglycan hydrolase activity as described herein. Such variants may result from, for example, genetic polymorphism or from human manipulation. Biologically active variants of a native HydH5 peptidoglycan hydrolase protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired HydH5 peptidoglycan hydrolase activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of HydH5 peptidoglycan hydrolase protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat. or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Bacterial Strains and Culture Conditions

Bacterial strains used to determine lytic spectrum of proteins are listed in Table 1. *S. aureus* Sa9 was used as the indicator strain for lytic activity (Obeso et al., supra). The *S. aureus* bovine isolates were from in house stocks (IPLA-CSIC), the *S. aureus* clinical isolates by Dr. Suárez (University of Oviedo, Spain), the *S. epidermidis* by Dr. Delgado (IPLA-CSIC) and the *S. aureus* MRSA strain N315 by Prof. Gabi Bierbaum (University of Bonn, Germany). All *Staphylococcus* strains were grown in TSB broth (Tryptic Soy Broth, DIFCO, Franklin Lakes, N.J.) at 37° C. with shaking or in TSB plates containing 2% (w/v) bacteriological agar (TSA). Other bacteria strains belonging to several different genera such as *Bacillus, Streptococcus, Listeria, Enterococcus, Clostridium, Lactococcus, Leuconostoc* and *Lactobacillus*, were insensitive to the lytic proteins (data not shown). *Bacillus, Streptococcus, Listeria* and *Enterococcus* strains were grown in 2×YT at 37° C. with shaking. *Clostridium* strain was grown in BHI (Brain Heart Infusion, Scharlau, Barcelona, Spain) at 30° C. under static conditions and anaerobiosis (Anaerocult A, Merck, Darmstadt, Germany). *Lactococcus* strain was grown in lactose-M17 (Scharlau, Barcelona, Spain) at 30° C. and static. *Leuconostoc* and *Lactobacillus* strains were grown in MRS (Scharlau, Barcelona, Spain) at 30° C. and static.

Example 2

Plasmid Constructs; DNA Manipulation

Bacteriophage vB_SauS-phiIPLA88 gene orf58 encoding HydH5 (Acc. Number ACJ64586) was codon-optimized (orf58-opt) based on the *E. coli* codon usage (Laird et al. 2005. *Protein Expr. Purif.* 39(2):237-246) and commercially synthesized (Genescript, Piscataway, N.J., USA). Then orf58-opt was synthesized with a 5' NdeI and a 3' XhoI restriction enzyme sites and the resultant fragment was subcloned between the NdeI and XhoI sites in the multi cloning site of the inducible expression vector pET21a (EMD Biosciences, San Diego, Calif.) which introduces a C-terminal 6×His-tag. All constructions in this work were created in this vector and thus have two additional amino acids residues introduced at the C-terminus corresponding to XhoI site (Leu-Glu) followed by the 6×His-tag. Truncated versions of HydH5 were constructed via PCR amplification by introducing cloning sites via the PCR primers: XhoI sites (underlined) after aa codon 156 for CHAP156 domain (CHAP156R: 5'-ACTGACTG<u>CTCGAG</u>TTT GTC-CGGGTG-3'; SEQ ID NO: 1) or after aa codon 166 for CHAP166 domain (CHAP166R: 5'-ATCGACTG <u>CTCGAG</u>TTTCGGCACCGG-3'; SEQ ID NO: 2) and a NdeI site before aa codon 475 for LYZ161 domain (LYZ161F: 5'-ACTGACTG <u>CATATG</u>GTTAGCGTCTCC-3'; SEQ ID NO: 3) or before aa codon 465 for LYZ171 domain (LYZ171F: 5'-ACT-GACTG<u>CATATG</u>CAAATGCTGAAC-3'; SEQ ID NO: 4). Forward primer for CHAP domains was pET21aBglII-F: 5'-CGTAGA GGATCGAGATCTCGATC-3' (SEQ ID NO: 5) and reverse primer for LYZ2 domains was pET21aStyI-R: 5'-CGT TTAGAGGCCCCAAGGGGTTATG-3' (SEQ ID NO: 6). The full-length lysostaphin gene was amplified with PCR pairs Full Lyso SalI-F (5'-ATC ATC <u>GTCGAC</u>GCTGCAACAC ATGAACATTCAGCAC-3'; SEQ ID NO: 7) and pET21aStyI-R. The lysostaphin fragment encoding the SH3b domain was amplified with PCR primer pairs Lyso SalI144-F (5'-GGAAAAGCA <u>GTCGAC</u>ACAGTAACTCC-3'; SEQ ID NO: 8) and pET21aStyI-R. These amplified fragments have an N-terminal SalI restriction site (underlined) designed to allow in-frame gene fusions of full-length lysostaphin or its SH3b domain individually to the C-terminus of HydH5 or its catalytic domain CHAP156. Vector constructs were performed in *E. coli* DH5α cells (Invitrogen, Carlsbad, Calif.) and induced in *E. coli* BL21 (DE3) (EMD Biosciences, San Diego, Calif.).

To determine whether both the CHAP and LYZ2 as single domains showed increased lytic activity toward *S. aureus* Sa9 over those previously obtained (Rodríguez et al. 2011.) four deletion constructs were generated. A schematic representation of all constructs is presented in FIG. 1. In order to ensure proper folding, each construct encoded a single lytic domain with an additional sequence of either 7 or 17 amino acids surrounding the catalytic domain (CHAP156, CHAP166, LYZ161 and LYZ171). In addition, due to the lack of a known cell wall binding domain in HydH5, we proceeded to determine whether the addition of a cell wall binding domain might increase the lytic activity of HydH5 and CHAP. Therefore, three different fusion proteins were created between lysostaphin and HydH5 (FIG. 1). Initially, the nucleic acid encoding the lysostaphin binding domain SH3b was fused to the nucleic acid encoding the full-length HydH5 protein, resulting in a protein with two catalytic domains and one cell wall binding domain, i.e., the protein HydH5-SH3b (SEQ ID NO: 10). A second construct was obtained by fusion of the nucleic acid encoding the CHAP156 domain to the nucleic acid encoding the lysostaphin SH3b domain resulting in the protein HydH5CHAP-SH3b (SEQ ID NO: 12). Finally, the nucleic acid encoding the full-length lysostaphin and the full-length HydH5 were fused in order to obtain the protein HydH5-Lysostaphin (SEQ ID NO: 14) with three catalytic domains and a cell wall binding domain. All the fusion proteins could be detected and purified with the exception of LYZ161 and LYZ171 whose products could not be detected after nickel column purification of the E. coli cultures.

The nucleic acid molecules encoding the constructs HydH5-SH3b, HydH5CHAP-SH3b, and HydH5-Lysostaphin, comprise nucleotides encoding C-terminal Leu-Glu-His-His-His-His-His-His residues and are identified by SEQ ID NOs: 9, 11, and 13, respectively. The expressed proteins are His-tagged with eight additional amino acid residues introduced at the C-terminus corresponding to the XhoI site (Leu-Glu) followed by six His residues. The proteins encoded by these nucleic acid sequences are identified by SEQ ID NOs: 10, 12 and 14, respectively. The constructs encoding CHAP156, CHAP166, LYZ161 and LYZ171 are identified by SEQ ID NOs: 15, 17, 19 and 21, respectively, and the resulting proteins, by SEQ ID NOs: 16, 18, 20 and 22, respectively.

Example 3

Protein Purification and Analysis

Protein purification was performed as previously described (Donovan and Foster-Frey, supra) with the following modifications: Exponential growing cultures induced by IPTG (1 mM, final concentration) were incubated at 10° C. for 20 h. Then 500 ml pellets where sonicated for 5 min using an automatic pulsing sonication (Bronson Sonifier; Bronson Sonic Power Co., Danbury, Conn., USA). Protein purification was carried out by NiNTA nickel column chromatography (Qiagen). Wash and elution profiles were empirically determined to be 20 ml of 10 mM imidazole, 40 ml of 20 mM imidazole and elution with 1 ml of 250 mM imidazole in phosphate buffered saline (50 mM $NaH_2PO_4$, 300 mM NaCl, pH 8.0) with 30% glycerol to prevent precipitation of the purified protein. Then all samples were converted to HydH5 activity buffer (HEPES 50 mM, NDSB-201 0.5 M, $CaCl_2$ 0.25 mM, $MnCl_2$ 0.25 mM, $MgCl_2$ 0.25 mM, TCEP 1 mM, NaCl 24 mM, KCl 1 mM pH 7.5) (Rodriguez et al. 2011.) containing 30% glycerol using pre-equilibrated Zeba Desalting Columns (Thermo Fisher Scientific, Rockford, Ill.).

Purity of HydH5 constructs were evaluated in a 15% (v/w) SDS-PAGE in Tris-Glycine buffer at 150 V for 1.5 h using Criterion Precast gels (Bio-Rad, Inc., Hercules, Calif.). The proteins purified on the nickel column retained the His tags, thus the His tags were present in the various assays. His tags can be removed by methods well known and practiced in the art.

Example 4

Zymogram, Plate Lysis and Turbidity Reduction Assays

Due to reports that peptidoglycan hydrolase lytic activity is not always quantitatively comparable between multiple assays although it usually agrees qualitatively (Kusuma and Kokai-Kun. 2005. *Antimicrob. Agents Chemother.* 49(8): 3256-3263), the lytic activities of the other proteins (HydH5, CHAP156, CHAP166, HydH5SH3b, CHAPSH3b and HydH5Lyso) were determined in three antimicrobial assays: zymogram, plate lysis and turbidity reduction assays. The turbidity reduction assay requires a robust enzyme in order to lyse large numbers of cells (starting concentration is $>10^9$ cells/ml), while the plate lysis assay can define relative activity with much lower amounts of bacteria, approximately $10^6$ cells.

Zymogram assays were performed as previously described (Rodríguez et al. 2011, supra). SDS gels were stained via conventional Coomassie staining and zymograms were soaked for 30 min in distilled water to remove SDS and then incubated at room temperature in water for 15 min to detect areas of clearing in the turbid gel where a lytic protein is localized.

Figure 2A:
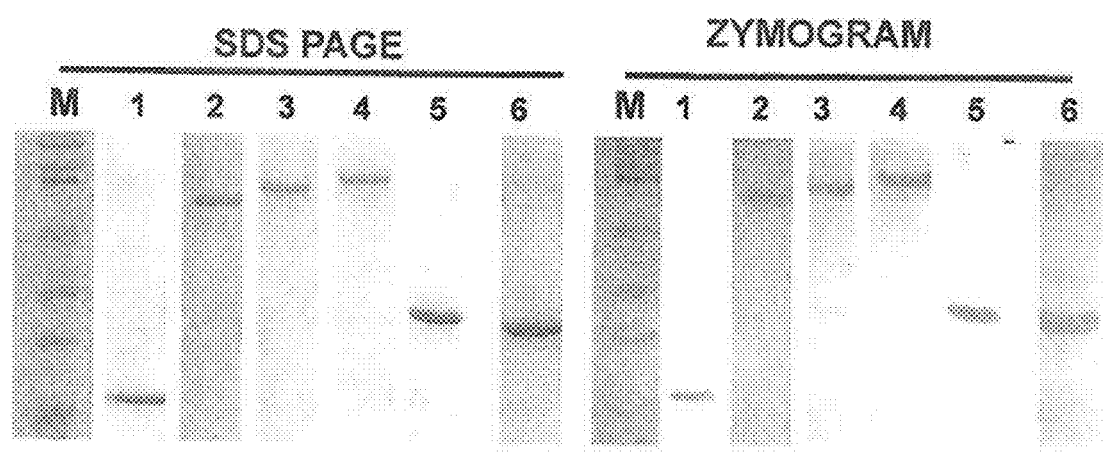
FIGS. 2A, 2B, and 2C depict the antimicrobial activity of the HydH5, deletion and fusion constructs.

As shown in FIG. 2A, all fusion proteins showed a single zone of clearing in the zymogram consistent with the predicted molecular mass and positions of the purified proteins in the SDS-PAGE. In addition, the truncation constructs (CHAP156 and CHAP166) also had the ability to lyse S. aureus. The activity of both truncated constructs (CHAP156 and CHAP166) turned out to be the same regardless of the length of the lytic domain. Therefore, only the results obtained with CHAP156 are shown.

Plate lysis was performed as previously described (Donovan and Foster-Frey, supra). Purified proteins for each construct were diluted in HydH5 activity buffer. Ten microliters of a 4 µM solution and 1:2 dilutions of each construct were spotted onto a freshly spread lawn of S. aureus Sa9, S. aureus MRSA N315 and the strains of Table 1 that had air dried for 30 min on tryptic soy agar plates. The spotted plates were air dried for 10 min in a laminar flow hood, and incubated overnight in a 37° C. environment. A cleared spot in the lawn indicates lysis of the pathogen. Scoring of the cleared spots occurred within 20 hr of plating the cells.

Figure 2B:
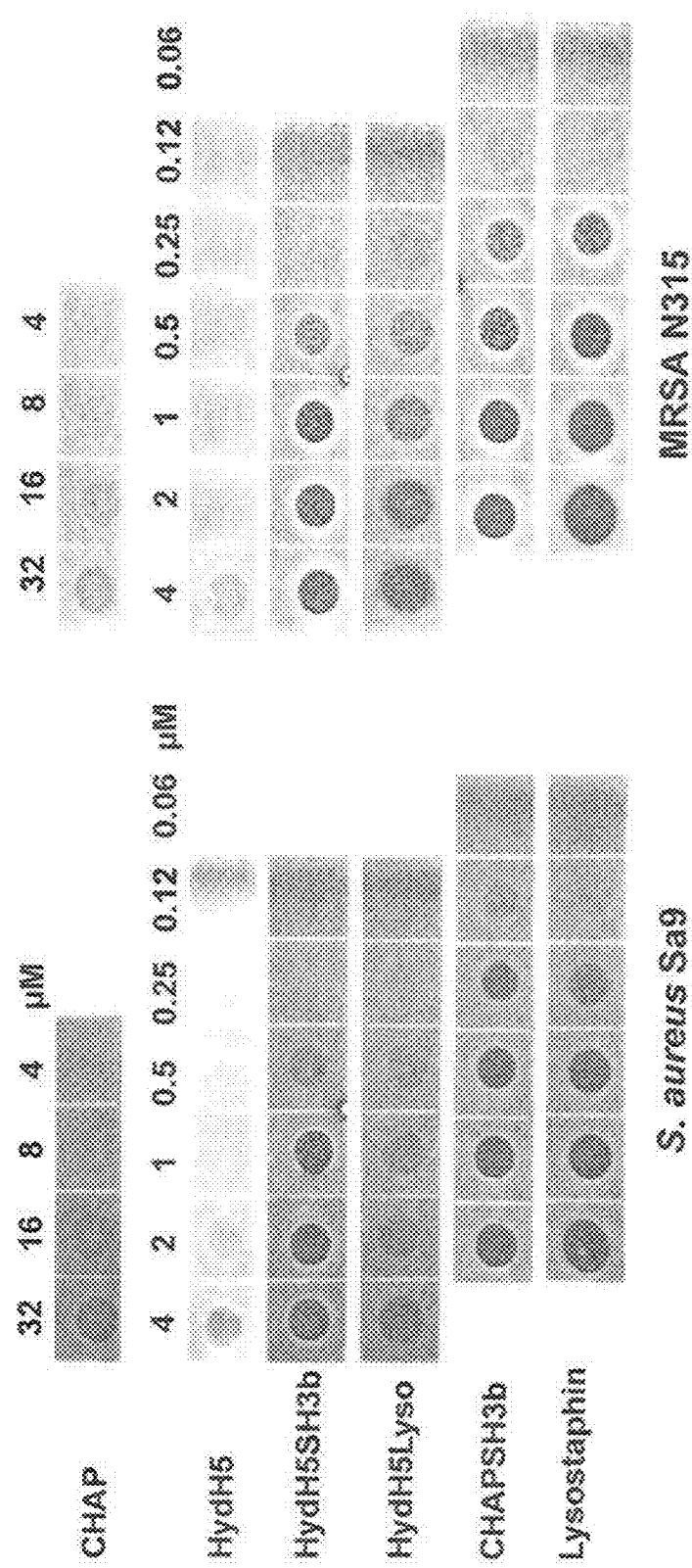

In the plate lysis assay (FIG. 2B) the full-length HydH5 showed clearing of S. aureus at ≥2 µM concentration while the HydH5CHAP domain required higher concentrations (≥16 µM). All the fusion proteins showed significantly greater activity than the parental protein HydH5, even against a methicillin-resistant S. aureus MRSA N315 strain. HydH5 has clear staphylolytic activity at 4 µM in contrast with fusion proteins which shown lysis activity at much lower concentrations (1 µM). Fusion of SH3b to the CHAP domain (HydH5CHAP-SH3b) also increased CHAP activity in plate lysis by a factor of 64.

In order to determine the specificity of the HydH5 and its derivative fusions, the plate lysis assay was performed using cells from different species and genera grown at $OD_{600\ nm}$=0.5. The different bacterial cells suspensions were exposed to 2 µM protein solutions in the plate lysis assay. We found that 10 µl of 2 µM HydH5-derived fusions, HydH5-SH3b and HydH5CHAP-SH3b, were able to lyse all S. aureus and S. epidermidis strains (14 tested; Table 1). In contrast, 10 µl of 2 µM HydH5-Lysostaphin was able to lyse all the S. aureus strains and only 2 out of 4 S. epidermidis strains. S. epidermidis lysis could be achieved at 4 µM (data not shown). Other bacteria belonging genera *Bacillus, Streptococcus, Clostridium, Lactococcus, Leuconostoc, Lactobacillus, Listeria* and *Enterococcus* were not affected by any of the staphylolytic proteins. The lytic activity of HydH5 and its derivative fusions is specific for staphylococci. It was observed that the degree of lytic activity on S. epidermidis strains was generally lower than that observed on S. aureus group. Moreover, a different spectrum of lytic activity was noted for each protein. HydH5 and HydH5-Lysostaphin seem to be the less active proteins in this assay. HydH5CHAP-SH3b showed the higher lytic activity even against S. epidermidis strains (Table 1). In addition to the differences between species, strain origin also seems to play a role in determining the lytic spectrum since HydH5-SH3b and HydH5-Lysostaphin were more active against bovine strains than clinical strains. This difference is more pronounced in the case of HydH5-Lysostaphin (Table 1).

TABLE 1

Lytic spectrum of HydH5 and its derivative fusions. Bacterial strains were exposed to 2 μM of each protein.

| STRAIN | PROTEIN | | | | |
|---|---|---|---|---|---|
| | HydH5 | HydH5Lyso | HydH5SH3b | CHAPSH3b | Lysostaphin |
| S. aureus: Bovine strains | | | | | |
| Sa9 | +* | ++ | +++ | +++ | +++ |
| Sa6 | − | +++ | +++ | +++ | +++ |
| Sa11 | + | +++ | +++ | +++ | +++ |
| AFG1 | + | ++ | +++ | +++ | +++ |
| AC9 | + | + | +++ | +++ | +++ |
| S. aureus: Human strains | | | | | |
| N315 | − | ++ | +++ | +++ | +++ |
| 96 | − | + | ++ | +++ | +++ |
| 143 | − | + | + | ++ | +++ |
| 445 | − | ++ | +++ | +++ | +++ |
| c4 | + | ++ | +++ | +++ | +++ |
| S. epidermidis | | | | | |
| B1CD2 | + | − | +++ | +++ | + |
| C213 | − | ++ | +++ | +++ | ++ |
| Z2LDC17 | + | + | ++ | +++ | − |
| SILDC3 | − | − | ++ | +++ | ++ |

*Strong lytic halo (+++), medium (++), weak (+) and no halo (−) was indicated.

Proteins were also tested by turbidity reduction assay (FIG. 2C) performed against live S. aureus Sa9 cells prepared as previously described (Donovan and Foster-Frey, supra; Becker et al. 2009, supra). The turbidity assay measures the drop in optical density (OD) resulting from lysis of the target bacteria with the HydH5-derived protein. A standardized turbidity assay modified from (Donovan et al. 2006a. Appl. Environ. Microbiol. 72:2988-2996) with S. aureus grown to logarithmic phase ($A_{600\ nm}$=0.4-0.6) at 37° C. in TSB (Tryptic Soy Broth, DIFCO, Franklin Lakes, N.J.) were performed in a 96 well dish and analyzed in a plate reader as described previously (Becker et al. 2009b, supra). Log phase cultures were harvested at 4° C. by centrifugation and stored on ice less than 4 hours until just before the assay when they were suspended in 150 mM NaCl, 10 mM Tris-Cl, pH 7.5 or 50 mM Phosphate buffer, pH 7.5 to an $A_{600\ nm}$ ~1.0. Enzyme samples are added to three wells of a 96 well dish in 100 μl of buffer (Ni-NTA elution buffer or storage buffer were shown to be equivalent). All samples are performed in triplicate. The assay is started by the addition of 100 μl of cells in buffer at $A_{600\ nm}$ ~1.0 via multichannel pipettor. A 'no enzyme control' of buffer and cells is included. $A_{600\ nm}$ readings are taken every 20 seconds for 5 minutes. The readings for each well are transferred electronically to an Excel spreadsheet where they are analyzed in a sliding window over each group of 3 consecutive time points during the five minute period, to identify the highest instantaneous change in $\Delta_{600\ nm}$ for each well. The absolute values of $\Delta A_{600\ nm}$ for each group of 3 time points are ranked and the optimum chosen based on highest absolute value and reproducibility in the triplicate wells. A similarly calculated buffer plus cells alone control value from triplicate wells is then subtracted from the highest ranked value for each experimental well, and the values for the triplicate wells averaged to give a $\Delta OD_{600\ nm}$/minute. This value is then divided by the concentration (μM) of enzyme protein in the sample tested to give a specific activity $\Delta OD_{600\ nm}$/μM/min. The turbidity reduction assays are repeated with multiple independent protein isolations to verify the results, but only representative assays are presented, due to the high day-to-day variability in the results, presumably due to variations in the cell culture preparations.

Figure 2C:
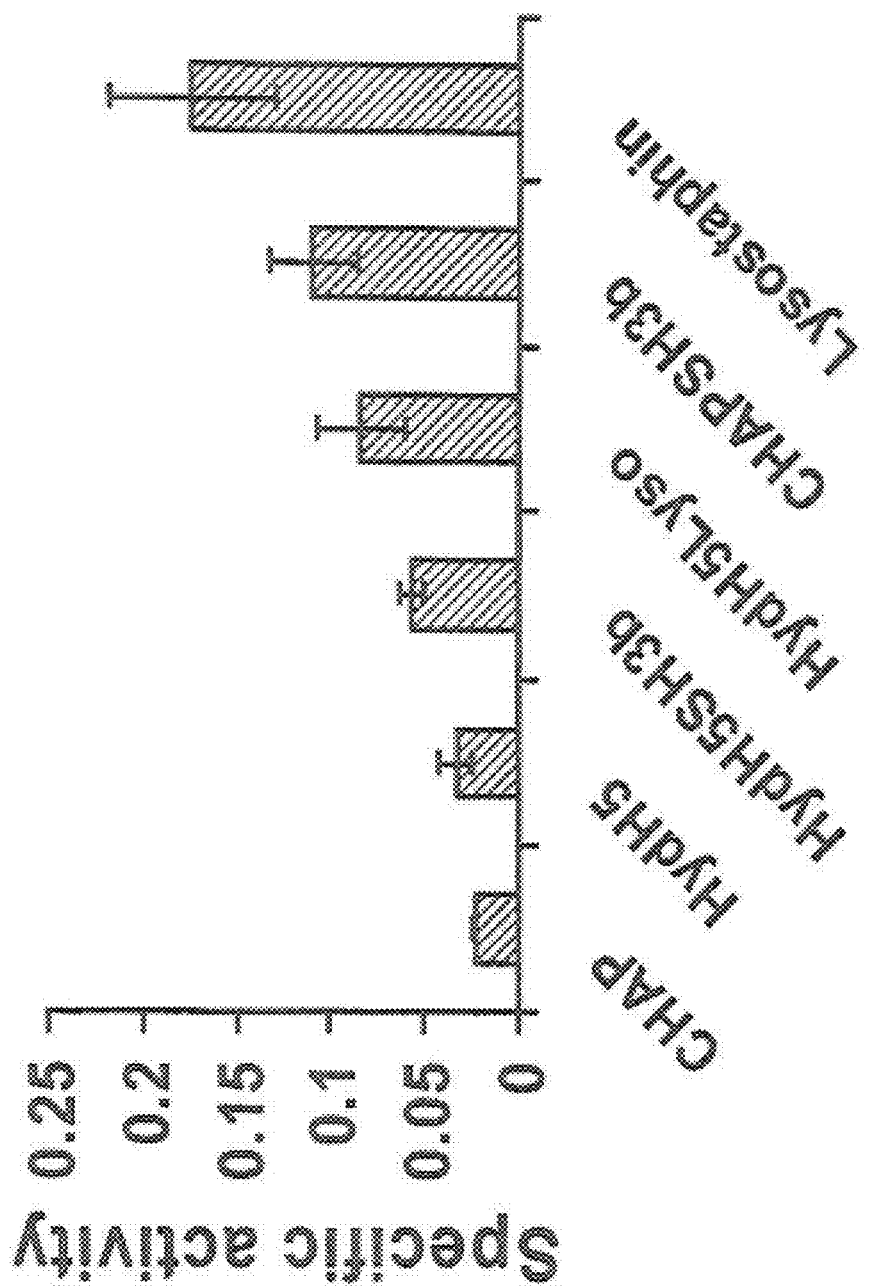

This assay was performed using 1 μM of purified proteins. Specific activity of the proteins was expressed as $\Delta OD_{600\ nm}$ $min^{-1}$ $\mu M^{-1}$. The full-length recombinant HydH5, synthesized from the E. coli codon optimized version of orf58opt, showed a lytic activity in this assay in contrast to that previously observed in HydH5 from the standard orf58 (Rodriguez et al. 2011, supra). The recombinant HydH5 was able to lyse live S. aureus Sa9 cells and had a specific activity of 0.033±0.009 $\Delta OD_{600\ nm}$ $min^{-1}$ $\mu M^{-1}$ (FIG. 2C). Similar results were obtained for HydH5CHAP domain but about 1.4-fold reduction in specific activity (0.023±0.001 $\Delta OD_{600\ nm}$ $min^{-1}$ $\mu M^{-1}$) was observed when compared to full-length HydH5 activity. Fusion proteins, HydH5-Lysostaphin and HydH5-SH3b, showed a 2.5- and 1.7-fold higher specific activity than the parental protein HydH5, respectively. HydH5CHAP-SH3b showed an activity 4.8-fold greater than the CHAP domain. The specific activity of HydH5CHAP-SH3b was calculated to be 0.109±0.023 $\Delta OD_{600\ nm}$ $min^{-1}$ $\mu M^{-1}$ the highest lytic activity obtained from HydH5 fusions. Therefore, C-terminal lysostaphin fusions conferred an enhanced staphylolytic activity to HydH5 and its catalytic domain CHAP.

Example 4

Synergy

To determine the interaction of HydH5 and its derivative fusions with the endolysin LysH5 a standard checkerboard dilution assay was performed using live S. aureus Sa9 cells in HydH5 activity buffer to a final $OD_{600\ nm}$ of ~0.8. Checkerboard tests were performed between LysH5 (Obeso et al., supra) and HydH5 and between LysH5 (Acc. Number EU573240) and HydH5-derived constructs as described in Garcia et al. (2010, supra)). Initially, we determined the minimum lytic concentration (MLC) of each protein: HydH5 (56.7 μg/ml), HydH5-Lysostaphin (12.5 μg/ml), HydH5-SH3b (13.5 μg/ml), HydH5CHAP-SH3b (8.7 μg/ml) and LysH5 (2.5 μg/ml). MLCs were defined as the lowest concentration at which an $OD_{600\ nm}$ less than 0.1 after 15 minutes of incubation at 37° C. was obtained. Ranges of enzyme concentrations were thus: LysH5 (2.5 μg/ml to 0.04 μg/ml); HydH5 (56.7 μg/ml to 0.06 μg/ml), HydH5-Lysostaphin (25.1 μg/ml to 0.02 μg/ml), HydH5-SH3b (13.5 μg/ml to 0.01 μg/ml) and HydH5CHAP-SH3b (17.34 μg/ml to 0.03 μg/ml). The fractional inhibitory concentration (FIC) was calculated as the minimum lytic concentration (MLC) of the antimicrobial in combination divided by the MLC of the antimicrobial acting alone. Strong synergy exists if the sum of the two FICs [ΣFIC=FICA+FICB] is <0.5 (Hall et al. 1983. J. Antimicrob. Chemother. 11(5):427-433). All the experiments were performed in duplicate.

Figure 3:
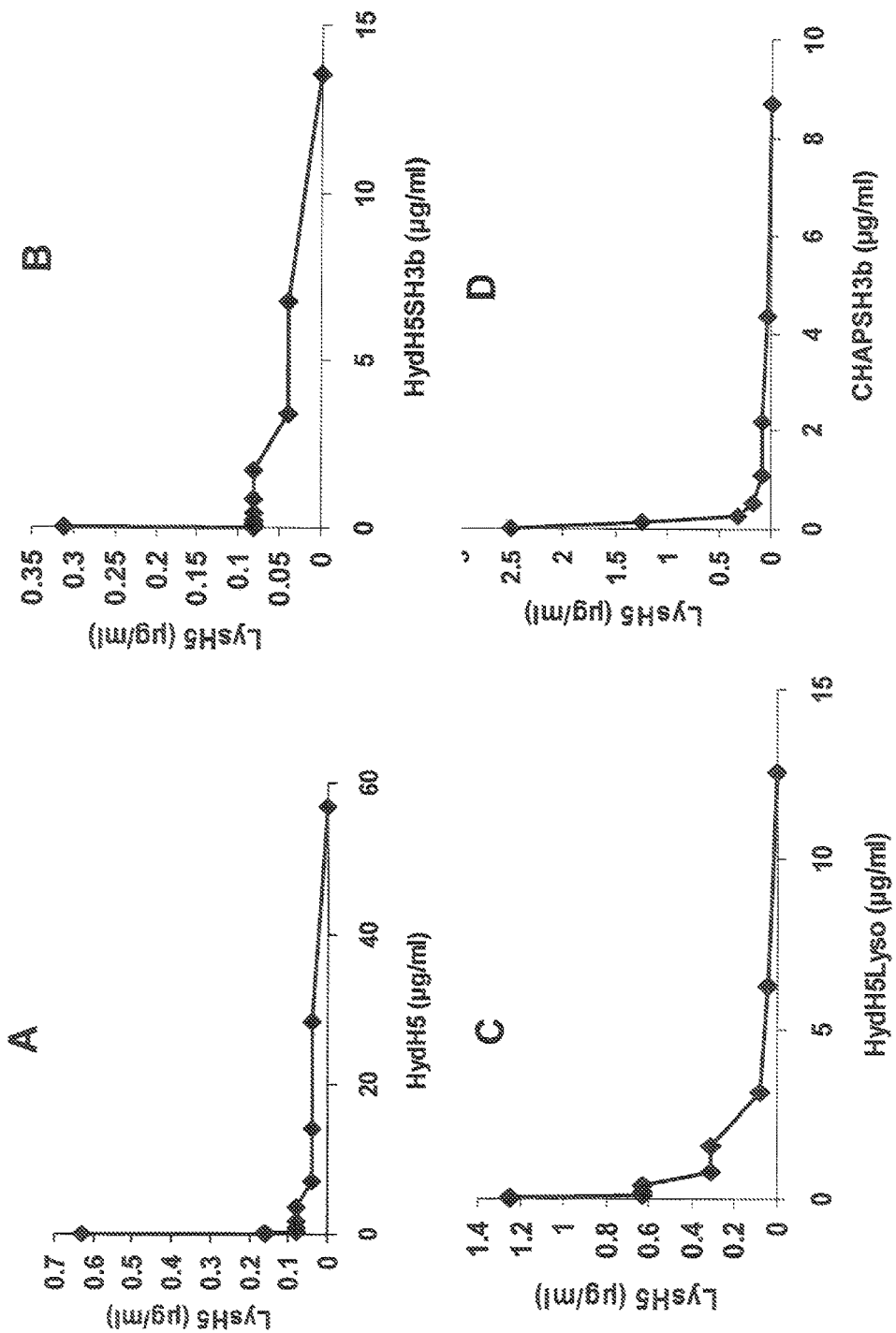
FIG. 3 shows the synergistic effect in checkerboard assay between endolysin LysH5 and HydH5 fusion constructs. Minimum Lytic Concentration (MLC) of each protein in the presence of subinhibitory concentrations of endolysin LysH5 is indicated. A (HydH5, 56.7 µg/ml to 0.06 µg/ml, ΣFIC 0.065±0.001), B (HydH5SH3b, 13.5 µg/ml to 0.01 µg/ml, ΣFIC 0.130±0.000), C (HydH5Lyso, 25.1 µg/ml to 0.02 µg/ml, ΣFIC 0.049±0.023), and D (CHAPSH3b, 17.34 µg/ml to 0.03 µg/ml, ΣFIC 0.063±0.022).

When HydH5 or its derived fusions were combined with LysH5, a synergistic effect was observed in all combinations. In the presence of subinhibitory concentrations of the HydH5-derived proteins, a lower endolysin LysH5 concentration was needed to fully decrease the S. aureus Sa9 $OD_{600}$ nm. Representative graphs of the synergistic interaction between LysH5 and HydH5 and between LysH5 and each HydH5-lysostaphin construct are shown in FIG. 3. HydH5 and its fusions act synergistically with LysH5 against *S. aureus*. From the MLC checkerboard test, the average ΣFIC values for the four protein combinations were calculated (FIG. 3). All these values are indicative of strong synergistic interaction and it could be concluded that the increased lysis observed with these mixtures would also be more effective to inhibit *S. aureus* bacterial growth.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated antimicrobial fusion peptidoglycan hydrolase protein, wherein said protein comprises SEQ ID NO:10, SEQ ID NO:12, or SEQ ID NO:14.

2. A composition useful for the treatment of disease caused by the *Staphylococcus* strains for which the fusion proteins of the invention are specific and effective, wherein said composition comprises the protein of claim 1 and a pharmaceutically acceptable carrier.

3. A composition useful for the treatment of disease caused by multidrug-resistant staphylococcal strains including methicillin resistant *S. aureus* (MRSA), wherein said composition comprises the protein of claim 1 and a pharmaceutically acceptable carrier.

4. A composition useful for the treatment of disease comprising the composition of claim 2 or claim 3 in combination with another sequence, or sequences, encoding one or more disease-resistance properties.

5. A kit, comprising a composition of any one of claims 2, 3 and 4.

* * * * *

```
                          SEQUENCE LISTING

<160> NUMBER OF SEQ ID NOS: 22

<210> SEQ ID NO 1
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 1
actgactgct cgagtttgtc cgggtg                                          26

<210> SEQ ID NO 2
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 2
atcgactgct cgagtttcgg caccgg                                          26

<210> SEQ ID NO 3
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 3
actgactgca tatggttagc gtctcc                                          26

<210> SEQ ID NO 4
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 4
actgactgca tatgcaaatg ctgaac                                          26

<210> SEQ ID NO 5
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 5
cgtagaggat cgagatctcg atc                                             23

<210> SEQ ID NO 6
```

```
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 6
cgtttagagg ccccaagggg ttatg                                          25

<210> SEQ ID NO 7
<211> LENGTH: 37
<212> TYPE: DNA
<213> ORGANISM: Artificial Sequence
<220> FEATURE:
<223> OTHER INFORMATION: Chemically Synthesized

<400> SEQUENCE: 7
atcatcgtcg acgctgcaac acatgaacat tcagcac                             37

<210> SEQ ID NO 8
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 8
ggaaaagcag tcgacacagt aactcc                                         26

<210> SEQ ID NO 9
<211> LENGTH: 2238
<212> TYPE: DNA
<213> ORGANISM: Unknown
<220> FEATURE:
<223> OTHER INFORMATION: vB_SauS-phiIPLA88 & Staphylococcus simulans

<400> SEQUENCE: 9
atgggcctgc cgaacccgaa agaccgtaaa ccgaccgcat cagaagtcgt tgaatgggca      60
ctgtacatgg ctaaaaatcg ccgtgtcatc gatgtcgacc gctcttatgg cggccagtgc     120
tgggatgtgc cgaactatat tctggaacgt tactggggct ttcgcacctg ggtaacgcg      180 aatgccatgg cacagaaatc caattatcgt ggccgcgatt ttaaaatcta ccgcaacacc     240
gcctcattca cgccgaaacc gggtgactgg gcagtttggg ctaaccgtaa tccgggccat     300
gtcgcaattg tggttggtcc ggcagataaa aatgcttttg tttctgtcga ccagaactgg     360
tataccgcga attggtcggg cagcccgccg tataaaatca acataccta ccacgatggt      420 ccgggcggtg ttacgcattt cgtccgtccg ccgtatcacc cggacaaaac caccccggca     480
ccgcagccgg tgccgaaacc gaaagatgac agtgatgaca agagaaaaa caacaaaaaa      540 gtgccgattt ggaaagatgt taaaaccatc aaatacacga ttagctctca ggtcgtgaac     600
tacccggaat acatctacca tttcatcgtg gaaggcaacc gtcgcctgga aaaaccgaaa     660
ggtattatga tccgtaatgc ccagaccatg agttccgttg aaaacctgta caattcccgc     720
aaaaaataca acaagatgt cgaatatccg catttttacg tggatcgtca caacatttgg      780
gccccgcgtc gcgcggtgtt tgaagttccg aatgaaccgg attatattgt catcgatgtg     840
tgtgaagact actctgcgag taaaaacgaa ttcatcttca cgaaatcta tgcaatgggc      900 gtggctgttg atatgatggt tgaatacgaa atcccgctgt caattgaaaa cctgaaagtc     960
gatgactcga tctggcgtag catgctggaa catgtgaact ggaatatgat tgataatggt    1020
gttccgccga agacaaaata tgaagcgctg gaaaagccc tgctgaacat ctttaaaaat     1080
```

```
cgtgaaaaac tgctgaactc gatcaccaaa ccgaccgtga cgaaaagccg cattaaagtc      1140
atggtggata caaaaatgc ggacattgcc aatgttcgtg attcatcgcc gacggcgaac       1200
aatggctccg cctcaaaaca gccgcaaatt atcaccgaaa cgagtccgta taccttcaaa      1260
caggccctgg atcgtcaaat gtcccgcggc aatccgaaaa atcacacac ctggggttgg       1320 gctaatgcca cccgtgcgca gacgagctct agtatgaacg tgaaacgcat ctgggaatcg      1380
aatacccagt gctatcaaat gctgaacctg ggcaaatacc agggtgttag cgtctcctca     1440
ctgaacaaaa ttctgaaagg caagggtacg ctgaacaatc agggtaaagc ctttgcagaa     1500
gcttgtaaaa aacataacat caacgaaatc tatctgattg cgcacgcctt tctggaaagc     1560
ggctacggta cctctaattt cgcaagtggc aaagatggtg tgtataacta ctttggcatc     1620
ggtgcttatg acaacaatcc gaattacgca atgaccttcg ctcgcaacaa aggctggacg    1680
tctccggcaa aagctattat gggcggtgcg agtttcgttc gtaaagatta catcaacaag    1740
ggtcagaaca ccctgtaccg tattcgctgg aacccgaaaa atccggcaac ccatcaatat    1800
gcgacggcca tcgaatggtg ccagcaccaa gcgagcacca ttgcgaaact gtataaacaa    1860
atcggtctga aggcgtcta cttcacccgc gacaaatata aactcgacac agtaactcca    1920
acgccgaata caggttggaa aacaaacaaa tatggcacac tatataaatc agagtcagct    1980
agcttcacac ctaatacaga tataataaca agaacgactg gtccatttag aagcatgccg    2040
cagtcaggag tcttaaaagc aggtcaaaca attcattatg atgaagtgat gaaacaagac    2100
ggtcatgttt gggtaggtta tacaggtaac agtggccaac gtatttactt gcctgtaaga    2160
acatggaata agtctactaa tactctgggt gttctgtggg gaactataaa gctcgagcac    2220
caccaccacc accactga                                                   2238
```

<210> SEQ ID NO 10
<211> LENGTH: 745
<212> TYPE: PRT
<213> ORGANISM: Unknown
<220> FEATURE:
<223> OTHER INFORMATION: vB_SauS-phiIPLA88 & Staphylococcus simulans

<400> SEQUENCE: 10

```
Met Gly Leu Pro Asn Pro Lys Asp Arg Lys Pro Thr Ala Ser Glu Val
1               5                   10                  15

Val Glu Trp Ala Leu Tyr Met Ala Lys Asn Arg Arg Val Ile Asp Val
                20                  25                  30

Asp Arg Ser Tyr Gly Gly Gln Cys Trp Asp Val Pro Asn Tyr Ile Leu
            35                  40                  45

Glu Arg Tyr Trp Gly Phe Arg Thr Trp Gly Asn Ala Asn Ala Met Ala
        50                  55                  60

Gln Lys Ser Asn Tyr Arg Gly Arg Asp Phe Lys Ile Tyr Arg Asn Thr
65                  70                  75                  80

Ala Ser Phe Thr Pro Lys Pro Gly Asp Trp Ala Val Trp Ala Asn Arg
                85                  90                  95

Asn Pro Gly His Val Ala Ile Val Gly Pro Ala Asp Lys Asn Ala
            100                 105                 110

Phe Val Ser Val Asp Gln Asn Trp Tyr Thr Ala Asn Trp Ser Gly Ser
        115                 120                 125

Pro Pro Tyr Lys Ile Lys His Thr Tyr His Asp Gly Pro Gly Gly Val
    130                 135                 140

Thr His Phe Val Arg Pro Pro Tyr His Pro Asp Lys Thr Thr Pro Ala
```

```
                145                 150                 155                 160
Pro Gln Pro Val Pro Lys Pro Lys Asp Asp Ser Asp Asp Lys Glu Lys
                    165                 170                 175

Asn Asn Lys Lys Val Pro Ile Trp Lys Asp Val Lys Thr Ile Lys Tyr
                    180                 185                 190

Thr Ile Ser Ser Gln Val Val Asn Tyr Pro Glu Tyr Ile Tyr His Phe
                    195                 200                 205

Ile Val Glu Gly Asn Arg Arg Leu Glu Lys Pro Lys Gly Ile Met Ile
                    210                 215                 220

Arg Asn Ala Gln Thr Met Ser Ser Val Glu Asn Leu Tyr Asn Ser Arg
225                 230                 235                 240

Lys Lys Tyr Lys Gln Asp Val Glu Tyr Pro His Phe Tyr Val Asp Arg
                    245                 250                 255

His Asn Ile Trp Ala Pro Arg Arg Ala Val Phe Glu Val Pro Asn Glu
                    260                 265                 270

Pro Asp Tyr Ile Val Ile Asp Val Cys Glu Asp Tyr Ser Ala Ser Lys
                    275                 280                 285

Asn Glu Phe Ile Phe Asn Glu Ile Tyr Ala Met Gly Val Ala Val Asp
                    290                 295                 300

Met Met Val Glu Tyr Glu Ile Pro Leu Ser Ile Glu Asn Leu Lys Val
305                 310                 315                 320

Asp Asp Ser Ile Trp Arg Ser Met Leu Glu His Val Asn Trp Asn Met
                    325                 330                 335

Ile Asp Asn Gly Val Pro Pro Lys Asp Lys Tyr Glu Ala Leu Glu Lys
                    340                 345                 350

Ala Leu Leu Asn Ile Phe Lys Asn Arg Glu Lys Leu Leu Asn Ser Ile
                    355                 360                 365

Thr Lys Pro Thr Val Thr Lys Ser Arg Ile Lys Val Met Val Asp Asn
                    370                 375                 380

Lys Asn Ala Asp Ile Ala Asn Val Arg Asp Ser Ser Pro Thr Ala Asn
385                 390                 395                 400

Asn Gly Ser Ala Ser Lys Gln Pro Gln Ile Ile Thr Glu Thr Ser Pro
                    405                 410                 415

Tyr Thr Phe Lys Gln Ala Leu Asp Arg Gln Met Ser Arg Gly Asn Pro
                    420                 425                 430

Lys Lys Ser His Thr Trp Gly Trp Ala Asn Ala Thr Arg Ala Gln Thr
                    435                 440                 445

Ser Ser Ser Met Asn Val Lys Arg Ile Trp Glu Ser Asn Thr Gln Cys
                    450                 455                 460

Tyr Gln Met Leu Asn Leu Gly Lys Tyr Gln Gly Val Ser Val Ser Ser
465                 470                 475                 480

Leu Asn Lys Ile Leu Lys Gly Lys Gly Thr Leu Asn Asn Gln Gly Lys
                    485                 490                 495

Ala Phe Ala Glu Ala Cys Lys Lys His Asn Ile Asn Glu Ile Tyr Leu
                    500                 505                 510

Ile Ala His Ala Phe Leu Glu Ser Gly Tyr Gly Thr Ser Asn Phe Ala
                    515                 520                 525

Ser Gly Lys Asp Gly Val Tyr Asn Tyr Phe Gly Ile Gly Ala Tyr Asp
                    530                 535                 540

Asn Asn Pro Asn Tyr Ala Met Thr Phe Ala Arg Asn Lys Gly Trp Thr
545                 550                 555                 560

Ser Pro Ala Lys Ala Ile Met Gly Gly Ala Ser Phe Val Arg Lys Asp
                    565                 570                 575
```

```
Tyr Ile Asn Lys Gly Gln Asn Thr Leu Tyr Arg Ile Arg Trp Asn Pro
            580                 585                 590

Lys Asn Pro Ala Thr His Gln Tyr Ala Thr Ala Ile Glu Trp Cys Gln
        595                 600                 605

His Gln Ala Ser Thr Ile Ala Lys Leu Tyr Lys Gln Ile Gly Leu Lys
610                 615                 620

Gly Val Tyr Phe Thr Arg Asp Lys Tyr Lys Leu Asp Thr Val Thr Pro
625                 630                 635                 640

Thr Pro Asn Thr Gly Trp Lys Thr Asn Lys Tyr Gly Thr Leu Tyr Lys
                645                 650                 655

Ser Glu Ser Ala Ser Phe Thr Pro Asn Thr Asp Ile Ile Thr Arg Thr
            660                 665                 670

Thr Gly Pro Phe Arg Ser Met Pro Gln Ser Gly Val Leu Lys Ala Gly
        675                 680                 685

Gln Thr Ile His Tyr Asp Glu Val Met Lys Gln Asp Gly His Val Trp
690                 695                 700

Val Gly Tyr Thr Gly Asn Ser Gly Gln Arg Ile Tyr Leu Pro Val Arg
705                 710                 715                 720

Thr Trp Asn Lys Ser Thr Asn Leu Gly Val Leu Trp Gly Thr Ile
                725                 730                 735

Lys Leu Glu His His His His His
            740                 745

<210> SEQ ID NO 11
<211> LENGTH: 804
<212> TYPE: DNA
<213> ORGANISM: Unknown
<220> FEATURE:
<223> OTHER INFORMATION: vB_SauS-phiIPLA88 & Staphylococcus simulans

<400> SEQUENCE: 11
atgggcctgc cgaacccgaa agaccgtaaa ccgaccgcat cagaagtcgt tgaatgggca      60
ctgtacatgg ctaaaaatcg ccgtgtcatc gatgtcgacc gctcttatgg cggccagtgc     120
tgggatgtgc cgaactatat tctggaacgt tactgggggct ttcgcacctg ggtaacgcg     180 aatgccatgg cacagaaatc caattatcgt ggccgcgatt ttaaaatcta ccgcaacacc     240
gcctcattca cgccgaaacc gggtgactgg gcagtttggg ctaaccgtaa tccgggccat     300
gtcgcaattg tggttggtcc ggcagataaa atgcttttg tttctgtcga ccagaactgg     360
tataccgcga attggtcggg cagcccgccg tataaaatca acataccta ccacgatggt     420 ccgggcggtg ttacgcattt cgtccgtccg ccgtatcacc cggacaaact cgacacagta     480
actccaacgc cgaatacagg ttggaaaaca acaaatatg gcacactata taatcagag      540 tcagctagct tcacacctaa tacagatata ataacaagaa cgactggtcc atttagaagc     600
atgccgcagt caggagtctt aaaagcaggt caaacaattc attatgatga agtgatgaaa     660
caagacggtc atgtttgggt aggttataca ggtaacagtg ccaacgtat ttacttgcct      720 gtaagaacat ggaataagtc tactaatact ctgggtgttc tgtggggaac tataaagctc     780
gagcaccacc accaccacca ctga                                             804

<210> SEQ ID NO 12
<211> LENGTH: 267
<212> TYPE: PRT
<213> ORGANISM: Unknown
<220> FEATURE:
<223> OTHER INFORMATION: vB_SauS-phiIPLA88 & Staphylococcus simulans
```

<400> SEQUENCE: 12

```
Met Gly Leu Pro Asn Pro Lys Asp Arg Lys Pro Thr Ala Ser Glu Val
1               5                   10                  15

Val Glu Trp Ala Leu Tyr Met Ala Lys Asn Arg Arg Val Ile Asp Val
            20                  25                  30

Asp Arg Ser Tyr Gly Gly Gln Cys Trp Asp Val Pro Asn Tyr Ile Leu
        35                  40                  45

Glu Arg Tyr Trp Gly Phe Arg Thr Trp Gly Asn Ala Asn Ala Met Ala
    50                  55                  60

Gln Lys Ser Asn Tyr Arg Gly Arg Asp Phe Lys Ile Tyr Arg Asn Thr
65                  70                  75                  80

Ala Ser Phe Thr Pro Lys Pro Gly Asp Trp Ala Val Trp Ala Asn Arg
                85                  90                  95

Asn Pro Gly His Val Ala Ile Val Val Gly Pro Ala Asp Lys Asn Ala
            100                 105                 110

Phe Val Ser Val Asp Gln Asn Trp Tyr Thr Ala Asn Trp Ser Gly Ser
        115                 120                 125

Pro Pro Tyr Lys Ile Lys His Thr Tyr His Asp Gly Pro Gly Gly Val
    130                 135                 140

Thr His Phe Val Arg Pro Pro Tyr His Pro Asp Lys Leu Asp Thr Val
145                 150                 155                 160

Thr Pro Thr Pro Asn Thr Gly Trp Lys Thr Asn Lys Tyr Gly Thr Leu
                165                 170                 175

Tyr Lys Ser Glu Ser Ala Ser Phe Thr Pro Asn Thr Asp Ile Ile Thr
            180                 185                 190

Arg Thr Thr Gly Pro Phe Arg Ser Met Pro Gln Ser Gly Val Leu Lys
        195                 200                 205

Ala Gly Gln Thr Ile His Tyr Asp Glu Val Met Lys Gln Asp Gly His
    210                 215                 220

Val Trp Val Gly Tyr Thr Gly Asn Ser Gly Gln Arg Ile Tyr Leu Pro
225                 230                 235                 240

Val Arg Thr Trp Asn Lys Ser Thr Asn Thr Leu Gly Val Leu Trp Gly
                245                 250                 255

Thr Ile Lys Leu Glu His His His His His His
            260                 265
```

<210> SEQ ID NO 13
<211> LENGTH: 2673
<212> TYPE: DNA
<213> ORGANISM: Unknown
<220> FEATURE:
<223> OTHER INFORMATION: vB_SauS-phiIPLA88 & Staphylococcus simulans

<400> SEQUENCE: 13

```
atgggcctgc cgaacccgaa agaccgtaaa ccgaccgcat cagaagtcgt tgaatgggca    60
ctgtacatgg ctaaaaatcg ccgtgtcatc gatgtcgacc gctcttatgg cggccagtgc   120
tgggatgtgc cgaactatat tctggaacgt tactggggct tcgcacctgg ggtaacgcg    180 aatgccatgg cacagaaatc caattatcgt ggccgcgatt ttaaaatcta ccgcaacacc   240
gcctcattca cgccgaaacc gggtgactgg gcagtttggg ctaaccgtaa tccgggccat   300
gtcgcaattg tggttggtcc ggcagataaa aatgcttttg tttctgtcga ccagaactgg   360
tataccgcga attggtcggg cagccgccg tataaaatca acataccta ccacgatggt    420 ccgggcggtg ttacgcattt cgtccgtccg ccgtatcacc cggacaaaac cacccccggca   480
```

```
ccgcagccgg tgccgaaacc gaaagatgac agtgatgaca agagaaaaa caacaaaaaa      540 gtgccgattt ggaaagatgt taaaaccatc aaatacacga ttagctctca ggtcgtgaac      600
tacccggaat acatctacca tttcatcgtg gaaggcaacc gtcgcctgga aaaaccgaaa      660
ggtattatga tccgtaatgc ccagaccatg agttccgttg aaaacctgta caattcccgc      720
aaaaaataca aacaagatgt cgaatatccg cattttacg tggatcgtca caacatttgg       780
gccccgcgtc gcgcggtgtt tgaagttccg aatgaaccgg attatattgt catcgatgtg      840
tgtgaagact actctgcgag taaaaacgaa ttcatcttca acgaaatcta tgcaatgggc      900
gtggctgttg atatgatggt tgaatacgaa atcccgctgt caattgaaaa cctgaaagtc      960
gatgactcga tctggcgtag catgctggaa catgtgaact ggaatatgat tgataatggt     1020
gttccgccga aagacaaata tgaagcgctg aaaaagccc tgctgaacat ctttaaaaat      1080
cgtgaaaaac tgctgaactc gatcaccaaa ccgaccgtga cgaaaagccg cattaaagtc     1140
atggtggata caaaaatgc ggacattgcc aatgttcgtg attcatcgcc gacggcgaac      1200
aatggctccg cctcaaaaca gccgcaaatt atcaccgaaa cgagtccgta ccttcaaa       1260 caggccctgg atcgtcaaat gtcccgcggc aatccgaaaa atcacacac ctggggttgg      1320 gctaatgcca cccgtgcgca gacgagctct agtatgaacg tgaaacgcat ctgggaatcg     1380
aatacccagt gctatcaaat gctgaacctg ggcaaatacc agggtgttag cgtctcctca     1440
ctgaacaaaa ttctgaaagg caagggtacg ctgaacaatc agggtaaagc cttgcagaa      1500 gcttgtaaaa aacataacat caacgaaatc tatctgattg cgcacgcctt tctggaaagc     1560
ggctacggta cctctaattt cgcaagtggc aaagatggtg tgtataacta ctttggcatc     1620
ggtgcttatg acaacaatcc gaattacgca atgaccttcg ctcgcaacaa aggctggacg     1680
tctccggcaa aagctattat gggcggtgcg agtttcgttc gtaaagatta catcaacaag     1740
ggtcagaaca ccctgtaccg tattcgctgg aacccgaaaa atccggcaac ccatcaatat     1800
gcgacggcca tcgaatggtg ccagcaccaa gcgagcacca ttgcgaaact gtataaacaa     1860
atcggtctga aaggcgtcta cttcacccgc gacaaatata acatatggc tgcaacacat     1920 gaacattcag cacaatggtt gaataattac aaaaaaggat atggttacgg cccttatcca     1980
ttaggtataa atggcggtat gcactacgga gttgattttt ttatgaatat tggaacacca     2040
gtaaaagcta tttcaagcgg aaaaatagtt gaagctggtt ggagtaatta cggaggaggt     2100
aatcaaatag gtcttattga aaatgatgga gtgcatagac aatggtatat gcatctaagt     2160
aaatataatt ttaaagtagg agattatgtc aaagctggtc aaataatcgg ttggtctgga     2220
agcactggtt attctacagc accacattta cacttccaaa gaatggttaa ttcattttca     2280
aattcaactg cccaagatcc aatgcctttc ttaaagagcg caggatatgg aaaagcaggt     2340
ggtacagtaa ctccaacgcc gaatacaggt tggaaaacaa acaaatatgg cacactatat     2400
aaatcagagt cagctagctt cacacctaat acagatataa taacaagaac gactggtcca     2460
tttagaagca tgccgcagtc aggagtctta aaagcaggtc aaacaattca ttatgatgaa     2520
gtgatgaaac aagacggtca tgtttgggta ggttatacag gtaacagtgg ccaacgtatt     2580
tacttgcctg taagaacatg gaataagtct actaatactc tgggtgttct gtggggaact     2640
ataaagctcg agcaccacca ccaccaccac tga                                   2673

<210> SEQ ID NO 14
<211> LENGTH: 890
<212> TYPE: PRT
```

<213> ORGANISM: Unknown
<220> FEATURE:
<223> OTHER INFORMATION: vB_SauS-phiIPLA88 & Staphylococcus simulans

<400> SEQUENCE: 14

```
Met Gly Leu Pro Asn Pro Lys Asp Arg Lys Pro Thr Ala Ser Glu Val
1               5                   10                  15

Val Glu Trp Ala Leu Tyr Met Ala Lys Asn Arg Arg Val Ile Asp Val
            20                  25                  30

Asp Arg Ser Tyr Gly Gly Gln Cys Trp Asp Val Pro Asn Tyr Ile Leu
        35                  40                  45

Glu Arg Tyr Trp Gly Phe Arg Thr Trp Gly Asn Ala Asn Ala Met Ala
    50                  55                  60

Gln Lys Ser Asn Tyr Arg Gly Arg Asp Phe Lys Ile Tyr Arg Asn Thr
65                  70                  75                  80

Ala Ser Phe Thr Pro Lys Pro Gly Asp Trp Ala Val Trp Ala Asn Arg
                85                  90                  95

Asn Pro Gly His Val Ala Ile Val Val Gly Pro Ala Asp Lys Asn Ala
            100                 105                 110

Phe Val Ser Val Asp Gln Asn Trp Tyr Thr Ala Asn Trp Ser Gly Ser
        115                 120                 125

Pro Pro Tyr Lys Ile Lys His Thr Tyr His Asp Gly Pro Gly Gly Val
    130                 135                 140

Thr His Phe Val Arg Pro Pro Tyr His Pro Asp Lys Thr Thr Pro Ala
145                 150                 155                 160

Pro Gln Pro Val Pro Lys Pro Lys Asp Ser Asp Asp Lys Glu Lys
                165                 170                 175

Asn Asn Lys Lys Val Pro Ile Trp Lys Asp Val Lys Thr Ile Lys Tyr
            180                 185                 190

Thr Ile Ser Ser Gln Val Val Asn Tyr Pro Glu Tyr Ile Tyr His Phe
        195                 200                 205

Ile Val Glu Gly Asn Arg Arg Leu Glu Lys Pro Lys Gly Ile Met Ile
    210                 215                 220

Arg Asn Ala Gln Thr Met Ser Ser Val Glu Asn Leu Tyr Asn Ser Arg
225                 230                 235                 240

Lys Lys Tyr Lys Gln Asp Val Glu Tyr Pro His Phe Tyr Val Asp Arg
                245                 250                 255

His Asn Ile Trp Ala Pro Arg Arg Ala Val Phe Glu Val Pro Asn Glu
            260                 265                 270

Pro Asp Tyr Ile Val Ile Asp Val Cys Glu Asp Tyr Ser Ala Ser Lys
        275                 280                 285

Asn Glu Phe Ile Phe Asn Glu Ile Tyr Ala Met Gly Val Ala Val Asp
    290                 295                 300

Met Met Val Glu Tyr Glu Ile Pro Leu Ser Ile Glu Asn Leu Lys Val
305                 310                 315                 320

Asp Asp Ser Ile Trp Arg Ser Met Leu Glu His Val Asn Trp Asn Met
                325                 330                 335

Ile Asp Asn Gly Val Pro Pro Lys Asp Lys Tyr Glu Ala Leu Glu Lys
            340                 345                 350

Ala Leu Leu Asn Ile Phe Lys Asn Arg Glu Lys Leu Leu Asn Ser Ile
        355                 360                 365

Thr Lys Pro Thr Val Thr Lys Ser Arg Ile Lys Val Met Val Asp Asn
    370                 375                 380

Lys Asn Ala Asp Ile Ala Asn Val Arg Asp Ser Ser Pro Thr Ala Asn
```

```
385                 390                 395                 400
Asn Gly Ser Ala Ser Lys Gln Pro Gln Ile Ile Thr Glu Thr Ser Pro
                405                 410                 415
Tyr Thr Phe Lys Gln Ala Leu Asp Arg Gln Met Ser Arg Gly Asn Pro
                420                 425                 430
Lys Lys Ser His Thr Trp Gly Trp Ala Asn Ala Thr Arg Ala Gln Thr
                435                 440                 445
Ser Ser Ser Met Asn Val Lys Arg Ile Trp Glu Ser Asn Thr Gln Cys
450                 455                 460
Tyr Gln Met Leu Asn Leu Gly Lys Tyr Gln Gly Val Ser Val Ser Ser
465                 470                 475                 480
Leu Asn Lys Ile Leu Lys Gly Lys Gly Thr Leu Asn Asn Gln Gly Lys
                485                 490                 495
Ala Phe Ala Glu Ala Cys Lys Lys His Asn Ile Asn Glu Ile Tyr Leu
                500                 505                 510
Ile Ala His Ala Phe Leu Glu Ser Gly Tyr Gly Thr Ser Asn Phe Ala
                515                 520                 525
Ser Gly Lys Asp Gly Val Tyr Asn Tyr Phe Gly Ile Gly Ala Tyr Asp
                530                 535                 540
Asn Asn Pro Asn Tyr Ala Met Thr Phe Ala Arg Asn Lys Gly Trp Thr
545                 550                 555                 560
Ser Pro Ala Lys Ala Ile Met Gly Gly Ala Ser Phe Val Arg Lys Asp
                565                 570                 575
Tyr Ile Asn Lys Gly Gln Asn Thr Leu Tyr Arg Ile Arg Trp Asn Pro
                580                 585                 590
Lys Asn Pro Ala Thr His Gln Tyr Ala Thr Ala Ile Glu Trp Cys Gln
                595                 600                 605
His Gln Ala Ser Thr Ile Ala Lys Leu Tyr Lys Gln Ile Gly Leu Lys
                610                 615                 620
Gly Val Tyr Phe Thr Arg Asp Lys Tyr Lys His Met Ala Ala Thr His
625                 630                 635                 640
Glu His Ser Ala Gln Trp Leu Asn Asn Tyr Lys Lys Gly Tyr Gly Tyr
                645                 650                 655
Gly Pro Tyr Pro Leu Gly Ile Asn Gly Gly Met His Tyr Gly Val Asp
                660                 665                 670
Phe Phe Met Asn Ile Gly Thr Pro Val Lys Ala Ile Ser Ser Gly Lys
                675                 680                 685
Ile Val Glu Ala Gly Trp Ser Asn Tyr Gly Gly Gly Asn Gln Ile Gly
                690                 695                 700
Leu Ile Glu Asn Asp Gly Val His Arg Gln Trp Tyr Met His Leu Ser
705                 710                 715                 720
Lys Tyr Asn Val Lys Val Gly Asp Tyr Val Lys Ala Gly Gln Ile Ile
                725                 730                 735
Gly Trp Ser Gly Ser Thr Gly Tyr Ser Thr Ala Pro His Leu His Phe
                740                 745                 750
Gln Arg Met Val Asn Ser Phe Ser Asn Ser Thr Ala Gln Asp Pro Met
                755                 760                 765
Pro Phe Leu Lys Ser Ala Gly Tyr Gly Lys Ala Gly Gly Thr Val Thr
                770                 775                 780
Pro Thr Pro Asn Thr Gly Trp Lys Thr Asn Lys Tyr Gly Thr Leu Tyr
785                 790                 795                 800
Lys Ser Glu Ser Ala Ser Phe Thr Pro Asn Thr Asp Ile Ile Thr Arg
                805                 810                 815
```

```
Thr Thr Gly Pro Phe Arg Ser Met Pro Gln Ser Gly Val Leu Lys Ala
            820                 825                 830
Gly Gln Thr Ile His Tyr Asp Glu Val Met Lys Gln Asp Gly His Val
            835                 840                 845
Trp Val Gly Tyr Thr Gly Asn Ser Gly Gln Arg Ile Tyr Leu Pro Val
            850                 855                 860
Arg Thr Trp Asn Lys Ser Thr Asn Thr Leu Gly Val Leu Trp Gly Thr
865                 870                 875                 880
Ile Lys Leu Glu His His His His His His
                885                 890

<210> SEQ ID NO 15
<211> LENGTH: 495
<212> TYPE: DNA
<213> ORGANISM: Unknown
<220> FEATURE:
<223> OTHER INFORMATION: vB_SauS-phiIPLA88  & Staphylococcus simulans

<400> SEQUENCE: 15
atgggcctgc cgaacccgaa agaccgtaaa ccgaccgcat cagaagtcgt tgaatgggca    60
ctgtacatgg ctaaaatcg ccgtgtcatc gatgtcgacc gctcttatgg cggccagtgc   120
tgggatgtgc cgaactatat tctggaacgt tactggggct tcgcacctg ggtaacgcg    180
aatgccatgc cacagaaatc caattatcgt ggccgcgatt ttaaaatcta ccgcaacacc   240
gcctcattca cgccgaaacc gggtgactgg gcagtttggg ctaaccgtaa tccgggccat   300
gtcgcaattg tggttggtcc ggcagataaa aatgcttttg tttctgtcga ccagaactgg   360
tataccgcga attggtcggg cagcccgccg tataaaatca acataccta ccacgatggt   420
ccgggcggtg ttacgcattt cgtccgtccg ccgtatcacc cggacaaact cgagcaccac   480
caccaccacc actga                                                    495

<210> SEQ ID NO 16
<211> LENGTH: 164
<212> TYPE: PRT
<213> ORGANISM: Unknown
<220> FEATURE:
<223> OTHER INFORMATION: vB_SauS-phiIPLA88

<400> SEQUENCE: 16

Met Gly Leu Pro Asn Pro Lys Asp Arg Lys Pro Thr Ala Ser Glu Val
1               5                   10                  15
Val Glu Trp Ala Leu Tyr Met Ala Lys Asn Arg Arg Val Ile Asp Val
            20                  25                  30
Asp Arg Ser Tyr Gly Gly Gln Cys Trp Asp Val Pro Asn Tyr Ile Leu
        35                  40                  45
Glu Arg Tyr Trp Gly Phe Arg Thr Trp Gly Asn Ala Asn Ala Met Ala
    50                  55                  60
Gln Lys Ser Asn Tyr Arg Gly Arg Asp Phe Lys Ile Tyr Arg Asn Thr
65                  70                  75                  80
Ala Ser Phe Thr Pro Lys Pro Gly Asp Trp Ala Val Trp Ala Asn Arg
                85                  90                  95
Asn Pro Gly His Val Ala Ile Val Val Gly Pro Ala Asp Lys Asn Ala
            100                 105                 110
Phe Val Ser Val Asp Gln Asn Trp Tyr Thr Ala Asn Trp Ser Gly Ser
        115                 120                 125
Pro Pro Tyr Lys Ile Lys His Thr Tyr His Asp Gly Pro Gly Gly Val
```

```
                  130                 135                 140
Thr His Phe Val Arg Pro Pro Tyr His Pro Asp Lys Leu Glu His His
145                 150                 155                 160

His His His His
```

```
<210> SEQ ID NO 17
<211> LENGTH: 525
<212> TYPE: DNA
<213> ORGANISM: Artificial Sequence
<220> FEATURE:
<223> OTHER INFORMATION: vB_SauS-phiIPLA88

<400> SEQUENCE: 17
atgggcctgc cgaacccgaa agaccgtaaa ccgaccgcat cagaagtcgt tgaatgggca      60
ctgtacatgg ctaaaaatcg ccgtgtcatc gatgtcgacc gctcttatgg cggccagtgc     120
tgggatgtgc cgaactatat tctggaacgt tactggggct ttcgcacctg ggtaacgcg     180
aatgccatgg cacagaaatc caattatcgt ggccgcgatt ttaaaatcta ccgcaacacc     240
gcctcattca cgccgaaacc gggtgactgg gcagtttggg ctaaccgtaa tccgggccat     300
gtcgcaattg tggttggtcc ggcagataaa aatgcttttg tttctgtcga ccagaactgg     360
tataccgcga attggtcggg cagcccgccg tataaaatca acataccta ccacgatggt     420
ccgggcggtg ttacgcattt cgtccgtccg ccgtatcacc cggacaaaac cacccgggca     480
ccgcagccgg tgccgaaact cgagcaccac caccaccacc actga                     525
```

```
<210> SEQ ID NO 18
<211> LENGTH: 174
<212> TYPE: PRT
<213> ORGANISM: Artificial Sequence
<220> FEATURE:
<223> OTHER INFORMATION: vB_SauS-phiIPLA88

<400> SEQUENCE: 18

Met Gly Leu Pro Asn Pro Lys Asp Arg Lys Pro Thr Ala Ser Glu Val
1               5                   10                  15

Val Glu Trp Ala Leu Tyr Met Ala Lys Asn Arg Arg Val Ile Asp Val
                20                  25                  30

Asp Arg Ser Tyr Gly Gly Gln Cys Trp Asp Val Pro Asn Tyr Ile Leu
            35                  40                  45

Glu Arg Tyr Trp Gly Phe Arg Thr Trp Gly Asn Ala Asn Ala Met Ala
        50                  55                  60

Gln Lys Ser Asn Tyr Arg Gly Arg Asp Phe Lys Ile Tyr Arg Asn Thr
65                  70                  75                  80

Ala Ser Phe Thr Pro Lys Pro Gly Asp Trp Ala Val Trp Ala Asn Arg
                85                  90                  95

Asn Pro Gly His Val Ala Ile Val Val Gly Pro Ala Asp Lys Asn Ala
            100                 105                 110

Phe Val Ser Val Asp Gln Asn Trp Tyr Thr Ala Asn Trp Ser Gly Ser
        115                 120                 125

Pro Pro Tyr Lys Ile Lys His Thr Tyr His Asp Gly Pro Gly Gly Val
    130                 135                 140

Thr His Phe Val Arg Pro Pro Tyr His Pro Asp Lys Thr Thr Pro Ala
145                 150                 155                 160

Pro Gln Pro Val Pro Lys Leu Glu His His His His His His
                165                 170
```

<210> SEQ ID NO 19
<211> LENGTH: 507
<212> TYPE: DNA
<213> ORGANISM: Artificial Sequence
<220> FEATURE:
<223> OTHER INFORMATION: vB_SauS-phiIPLA88

<400> SEQUENCE: 19

```
atggttagcg tctcctcact gaacaaaatt ctgaaaggca agggtacgct gaacaatcag      60
ggtaaagcct ttgcagaagc ttgtaaaaaa cataacatca acgaaatcta tctgattgcg     120
cacgcctttc tggaaagcgg ctacggtacc tctaatttcg caagtggcaa agatggtgtg     180
tataactact ttggcatcgg tgcttatgac aacaatccga attacgcaat gaccttcgct     240
cgcaacaaag ctggacgtc tccggcaaaa gctattatgg gcggtgcgag tttcgttcgt     300
aaagattaca tcaacaaggg tcagaacacc ctgtaccgta ttcgctggaa cccgaaaaat     360
ccggcaaccc atcaatatgc gacggccatc gaatggtgcc agcaccaagc gagcaccatt     420
gcgaaactgt ataaacaaat cggtctgaaa ggcgtctact tcacccgcga caaatataaa     480
ctcgagcacc accaccacca ccactga                                         507
```

<210> SEQ ID NO 20
<211> LENGTH: 168
<212> TYPE: PRT
<213> ORGANISM: Artificial Sequence
<220> FEATURE:
<223> OTHER INFORMATION: vB_SauS-phiIPLA88

<400> SEQUENCE: 20

```
Met Val Ser Val Ser Ser Leu Asn Lys Ile Leu Lys Gly Lys Gly Thr
1               5                   10                  15

Leu Asn Asn Gln Gly Lys Ala Phe Ala Glu Ala Cys Lys Lys His Asn
            20                  25                  30

Ile Asn Glu Ile Tyr Leu Ile Ala His Ala Phe Leu Glu Ser Gly Tyr
        35                  40                  45

Gly Thr Ser Asn Phe Ala Ser Gly Lys Asp Gly Val Tyr Asn Tyr Phe
    50                  55                  60

Gly Ile Gly Ala Tyr Asp Asn Asn Pro Asn Tyr Ala Met Thr Phe Ala
65                  70                  75                  80

Arg Asn Lys Gly Trp Thr Ser Pro Ala Lys Ala Ile Met Gly Gly Ala
                85                  90                  95

Ser Phe Val Arg Lys Asp Tyr Ile Asn Lys Gly Gln Asn Thr Leu Tyr
            100                 105                 110

Arg Ile Arg Trp Asn Pro Lys Asn Pro Ala Thr His Gln Tyr Ala Thr
        115                 120                 125

Ala Ile Glu Trp Cys Gln His Gln Ala Ser Thr Ile Ala Lys Leu Tyr
    130                 135                 140

Lys Gln Ile Gly Leu Lys Gly Val Tyr Phe Thr Arg Asp Lys Tyr Lys
145                 150                 155                 160

Leu Glu His His His His His His
                165
```

<210> SEQ ID NO 21
<211> LENGTH: 537
<212> TYPE: DNA
<213> ORGANISM: Artificial Sequence
<220> FEATURE:
<223> OTHER INFORMATION: vB_SauS-phiIPLA88

<400> SEQUENCE: 21

```
atgcaaatgc tgaacctggg caaataccag ggtgttagcg tctcctcact gaacaaaatt    60
ctgaaaggca agggtacgct gaacaatcag ggtaaagcct ttgcagaagc ttgtaaaaaa   120
cataacatca acgaaatcta tctgattgcg cacgcctttc tggaaagcgg ctacggtacc   180
tctaatttcg caagtggcaa agatggtgtg tataactact ttggcatcgg tgcttatgac   240
aacaatccga attacgcaat gaccttcgct cgcaacaaag gctggacgtc tccggcaaaa   300
gctattatgg gcggtgcgag tttcgttcgt aaagattaca tcaacaaggg tcagaacacc   360
ctgtaccgta ttcgctggaa cccgaaaaat ccggcaaccc atcaatatgc gacggccatc   420
gaatggtgcc agcaccaagc gagcaccatt gcgaaactgt ataaacaaat cggtctgaaa   480
ggcgtctact tcacccgcga caaatataaa ctcgagcacc accaccacca ccactga      537
```

<210> SEQ ID NO 22
<211> LENGTH: 178
<212> TYPE: PRT
<213> ORGANISM: Artificial Sequence
<220> FEATURE:
<223> OTHER INFORMATION: vB_SauS-phiIPLA88

<400> SEQUENCE: 22

```
Met Gln Met Leu Asn Leu Gly Lys Tyr Gln Gly Val Ser Val Ser Ser
1               5                   10                  15

Leu Asn Lys Ile Leu Lys Gly Lys Gly Thr Leu Asn Asn Gln Gly Lys
            20                  25                  30

Ala Phe Ala Glu Ala Cys Lys Lys His Asn Ile Asn Glu Ile Tyr Leu
        35                  40                  45

Ile Ala His Ala Phe Leu Glu Ser Gly Tyr Gly Thr Ser Asn Phe Ala
    50                  55                  60

Ser Gly Lys Asp Gly Val Tyr Asn Tyr Phe Gly Ile Gly Ala Tyr Asp
65                  70                  75                  80

Asn Asn Pro Asn Tyr Ala Met Thr Phe Ala Arg Asn Lys Gly Trp Thr
                85                  90                  95

Ser Pro Ala Lys Ala Ile Met Gly Gly Ala Ser Phe Val Arg Lys Asp
            100                 105                 110

Tyr Ile Asn Lys Gly Gln Asn Thr Leu Tyr Arg Ile Arg Trp Asn Pro
        115                 120                 125

Lys Asn Pro Ala Thr His Gln Tyr Ala Thr Ala Ile Glu Trp Cys Gln
    130                 135                 140

His Gln Ala Ser Thr Ile Ala Lys Leu Tyr Lys Gln Ile Gly Leu Lys
145                 150                 155                 160

Gly Val Tyr Phe Thr Arg Asp Lys Tyr Lys Leu Glu His His His His
                165                 170                 175

His His
```